United States Patent [19]
Casipit et al.

[11] Patent Number: 6,127,524
[45] Date of Patent: Oct. 3, 2000

[54] BINDING MOLECULES AND COMPUTER-BASED METHODS OF INCREASING THE BINDING AFFINITY THEREOF

[75] Inventors: Clayton L. Casipit, Hialeah; Hing C. Wong; Bee Y. Huang, both of Fort Lauderdale, all of Fla.

[73] Assignee: Dade Behring Inc., Deerfield, Ill.

[21] Appl. No.: 08/732,708

[22] Filed: Oct. 18, 1996

[51] Int. Cl.$^7$ .................................................. A61K 39/395
[52] U.S. Cl. ................................. 530/387.3; 530/388.25; 424/133.1; 424/152.1; 435/71.1
[58] Field of Search ..................................... 435/455, 337, 435/71.1; 530/387.3, 388.25; 424/133.1, 152.1

[56] References Cited

U.S. PATENT DOCUMENTS

| | | |
|---|---|---|
| 4,853,871 | 8/1989 | Pantoliano et al. . |
| 5,071,954 | 12/1991 | Pelzer et al. . |

FOREIGN PATENT DOCUMENTS

| | | |
|---|---|---|
| 589840A1 | 3/1994 | France . |
| WO 91/17177 | 11/1991 | WIPO . |
| WO 93/22436 | 11/1993 | WIPO . |
| WO 94/04679 | 3/1994 | WIPO . |

OTHER PUBLICATIONS

Lewin Science vol. 237 1570, 1987.
Reeck et al Cell vol. 50 667, 1987.
Groves et al Hybridoma vol. 6(1) 71, 1987.
Rudikoff et al Proc Natl Acad Sci USA vol. 79 1979, 1982.
Panka et al proc Natl Acad Sci USA vol. 85 3080, May 1988.
Amit Science col. 233 747, 1986.
J. Novotny, et al., *Biochemistry* 28: 4735–4749 (1989).
P.R. Stenzel–Johnson, et al., *Biochemistry* 33: 14400–14406 (1994).
R. Near et al. "Heavy and Light Chain Contributions to Antigen Binding in an Anti–Digoxin Chain Recombinant Antibody Produced by Transfection of Cloned Anti–Digoxin Antibody Genes", *Molecular Immunology*, vol. 27, No. 9, pp. 901–909, 1990.
U. Schulze–Gahment et al. "Detailed Analysis of the Free and Bound Conformations of an Antibody", *J. Mol. Biol.* vol. 234, pp. 1098–1118, 1993.
S. J. Searle et al. "Antibody Structure and Function", *Antibody Engineering*, pp. 4–47, 1995.
K. G. Mann et al. "Cofactor Proteins in the Assembly and Expression of Blood Clotting Enzyme Complexes", *Ann. Rev. Biochem.* vol. 57, pp. 915–950, 1988.
S. Ruff–Jamison et al. "Molecular Modeling and site–directed mutagenesis of an anti–phosphotyrosine antibody predicts the combining site and allows the detection of higher affinity interactions", *Protein Engineering*, vol. 6, No. 6, pp. 661–668, 1993.
S. Roberts et al. "Generation of an Antibody with Enhanced affinity and specificity for its antigen by protein engineering", *Nature*, vol. 328, pp. 731–734, Aug. 1987.

J. M. Rini et al. "Structural Evidence for Induced Fit as a Mechanism for Antibody–Antigen Recognition", *Science*, vol. 255, pp. 959–965, Feb. 1992.
R. Near et al. "Characterization of an Anti–Digoxin Antibody Binding Site by Site–Directed In Vitro Mutagenesis", *Molecular Immunology*, vol. 30, No. 4, pp. 369–377, 1993.
R. Kelley, et al. "Thermodymanic Analysis of an Antibody Functional Epitope", *Biochemistry*, No. 32, pp. 6828–6835, 1993.
H. J. Dyson et al. "Antigenic peptides", *The FASEB Journal*, vol. 9, pp. 37–42, Jan. 1995.
L.K. Denzin et al. "Single–chain Site–specific Mutations of Fluorescein–Amino Acid Contact Residues in High Affinity Monoclonal Antibody 4–4–20", *The Journal of Biological Chemistry*, vol. 266, No. 21, pp. 14095–14103, Jul. 1991.
P. de la Paz et al. "Modeling of the Combining Sites of Three Anti–Lysozyme Monoclonal Antibodies and of the Complex Between One of the Antibodies and Its Epitope", *The EMBO Journal*, vol. 5 No. 2, pp. 415–425, 1986.
C. Chothia et al. "Conformations of Immunoglobulin Hypervariable Regions", *Nature*, vol. 342, pp. 877–883, Dec. 1989.
R. E. Bruccoleri et al. "Structure of Antibody Hypervariable Loops Reproduced by a Conformational Search Algorithm", *Nature*, vol. 335, pp. 564–568, Oct. 1988.
B. Braden et al. "Three–Dimensional Structures of the Free and the Antigen–Complexed Fab form Monoclonal Anti–lysozyme Antibody D44.1", *J. Mol. Biol.*, vol. 243, pp. 767–781, 1994.
B. Braden et al. "Structural Features of the Reactions Between Antibodies and Protein Antigens", *The FASEB Journal*, Structure of Antigen–Antibody Complexes, Reviews, No. 9, pp. 9–16, 1995.
A.G. Amit et al. "Three–Dimensional Structure of an Antigen–Antibody Complex of 2.8 Å Resolution", *Science*, vol. 233, pp. 747–753, Aug. 1986.
D. Altschuh et al. "Determination of Kinetic Constants for the Interaction between a Monoclonal Antibody and Peptides Using Surface Plasmon Resonance", *Biochemistry*, vol. 31, No. 27, pp. 6298–6304, 1992.
P. H. Walls et al. "New Algorithm to Model Protein—Protein Recognition Based on Surface Complementarity", *J. Mol. Biol.*, vol. 228, pp. 277–297, 1992.

(List continued on next page.)

*Primary Examiner*—Julie Burke
*Attorney, Agent, or Firm*—Robert L. Buchanan; Peter F. Corless; Dike, Bronstein, Roberts & Cushman, LLP

[57] ABSTRACT

The present invention features novel binding molecules and methods of improving the specific binding affinity of binding molecules, which methods do not use X-ray crystallography. For example, in one aspect, the invention features methods of making antibodies with improved specific binding affinity for a polypeptide produced during prothrombin activation. The present invention is useful for a variety of applications including, e.g., producing binding molecules with improved binding affinity; and screening for binding molecules which are in low abundance.

4 Claims, 20 Drawing Sheets

OTHER PUBLICATIONS

D. Wang et al. "The Repertoire of Antibodies to a Single Antigenic Determinant", *Molecular Immunology*, vol. 28, No. 12, pp. 1387–1397, 1991.

V. Wittman et al. "Regulation of the Penicillinase Genes of *Bacillus licheniformis*: Interaction of the pen Repressor with Its Operators", *Journal of Bacteriology*, vol. 170, No. 7, pp. 3206–3212, Jul. 1988.

M. Totrov et al. "Detailed ab inition Prediction of Lysozyme–antibody Complex with 1.6 Å accuracy", *Structural Biol.*, vol. 1 No. 4, pp. 259–263, Apr. 1994.

N. Verdaguer et al. "Structure of the Major Antigenic Loop of Foot–and–mouth Disease Virus complexed with a Neutralizing Antibody: Direct Involvement of the Arg–Gly–Asp Motif in the Interaction", *The EMBO Journal*, vol. 14, No. 8, pp. 1690–1695, 1995.

R. K. Strong " Three–Dimensional Structure of Murine Anti–p–azophenylarsonate Fab 36–71. 1. X–ray Crystallography, Site–Directed Mutagenesis, and Modeling of the Complex with Hapten", *Biochemistry*, vol. 30, No. 15, 1991.

R. L. Stanfield et al. "Crystal Structures of an Antibody to a Peptide and Its Complex with Peptide Antigen at 2.8 Å", *Science*, vol. 248, pp. 712–719, May 1990.

J. Sharon "Structural Correlates of High Antibody Affinity: Three Engineered Amino Acid Substitutions Can Increase the Affinity of an Anti–pazophenylar–sonate Antibody 200–fold", *Proc. Natl. Acad. Sci.*, vol. 87, pp. 4814–4817, Jun. 1990.

D. Fremont et al. "Structures of an MHC Class II Molecule with Covalently Bound Single Peptides", *Science*, vol. 272, pp. 1000–1004, May 1996.

L. Essen et al. "The de Novo Design of an Antibody Combining Site Crystallographic Analysis of the $V_L$ Domain Confirms the Structural Model", *J. Mol. Biol.* vol. 238, pp. 226–244, 1994.

S. Dubel et al. "Bifunctional and Multimeric Complexes of Streptavidin Fused to Single Chain Antibodies (scFv)", *Journal of Immunological Methods*, Elservier Science B. V., vol. 178, pp. 201–209, 1995.

A. Skerra et al. "Structural Features of the McPC603 $F_{ab}$ Fragment not Defined in the X–ray Structure", *FEBS*, vol. 271, No. 1, 2, pp. 203–206, Oct. 1990.

A. Pluckthun et al. "Fengineering of Antibodies with a Known Three–dimensional Structure", *Cold Spring Harbor Symposia on Quantitative Biology. Antibody Engineering*, vol. LII, pp. 105–112, 1987.

S. Borman "Scientists Refine Understanding of Protein Folding and Design", *C&EN*, May 27, 1996, pp. 2935.

FIG. 1

```
EcoR V
GATATC T TCA GCT TCC AGC AGT GAT ATT GTG ATG ACT CAG GCT GCA CCC TCA ATA CCT GTC ACT CCT GGA
       D   I   V   M   T   Q   A   A   P   S   I   P   V   T   P   G

GAG TCA GTA TCC ATC TCC TGC
 E   S   V   S   I   S   C
                                                    L1
AGG TCT AGT AAG AGT CTC | CTG | CAT AGT AAT GGC AAC ACT | TTG TAT
 R   S   S   K   S   L  |  L  |  H   S   N   G   N   T |  L   Y
                        |  A  |                         |  A
                        |     |                         |  F

TGG TTC CTG CAG AGG CCA GGC CAG TCT CCT CAG CTC CTG ATA TAT
 W   F   L   Q   R   P   G   Q   S   P   Q   L   L   I   Y
                                        L2
CGG | ATG TCC AAC CTT GCC TCA | GGA GTC CTA GGC AGG GTC AGT GGC AGT GGG TCA GGA ACT GAT TTC ACA CTG AGA ATC AGT AGA GTG GAG GCT
 R  |  M   S   N   L   A   S |  G   V   L   G   R   V   S   G   S   G   S   G   T   D   F   T   L   R   I   S   R   V   E   A
 A  |  K                      |
                                                           L3
GAG GAT ATG GGG GTT TAT TAC TGT TTG CAG | CAT | CTA GAA | TTT | CCG CTC ACG
 E   D   M   G   V   Y   Y   C   L   Q |  H  |  L   E  |  F  |  P   L   T
                                        |  A  |        |  A  |
                                        |     |        |  Y  |

TTC GGT GCT GGG ACC AGG CTG GAG CTG AAA CGT AAGTAG CGGCCG    Eag I
 F   G   A   G   T   R   L   E   L   K   R   K
```

EcoR V
GATATC ACA GGT GTC CTC TCT GAG GTT CAG CTG CAG CAG TCT GGG GCT GAG CTT GTG AGG CCA GGG GCC TTA
       E   T   G   V   L   S   E   V   Q   L   Q   Q   S   G   A   E   L   V   R   P   G   A   L

GTC AAG TTG TCC TGC AAA GCT TCT GGC TTC AAC ATT AAA GAC TAC TAT ATG CAC
 V   K   L   S   C   K   A   S   G   F   N   I   K   D   Y   Y   M   H
                                 |_____|
                                                 H1

TGG GTG AAG CAG AGG CCT GAA CAG GGC CTG GAG TGG ATT GGA
 W   V   K   Q   R   P   E   Q   G   L   E   W   I   G
 ___
|ATT GAT CCT GAT AAT GGT GAA ACT ATA TAT GAC CCG AAG TTT CAG GGC
  I   D   P   D   N   G   E   T   I   Y   D   P   K   F   Q   G|
  W   A                                                         H2
  Y

AAG GCC AGT ATA ACA GCA GAC ACA TCT TCC AAC ACA GCC TAT CTG CAG CTC AGC AGC CTG ACA TCT GAG GAC
 K   A   S   I   T   A   D   T   S   S   N   T   A   Y   L   Q   L   S   S   L   T   S   E   D

ACT GCC GTC TAT TAC TGT GAC
 T   A   V   Y   Y   C   D
                         ___
                        |TAT TAT AGG TTC GAC GAC|TAT GCT GTG GAC TAC|
                         Y   Y   R   F   D   D | Y   A   V   D   Y |
                         A                     | P                 |
                                                        H3

TGG GGT CAA GGA ACC TCA GTC ACC GTC TCC TCA GGTAAGA CGGCCG
 W   G   Q   G   T   S   V   T   V   S   S              EagI

FIG.2

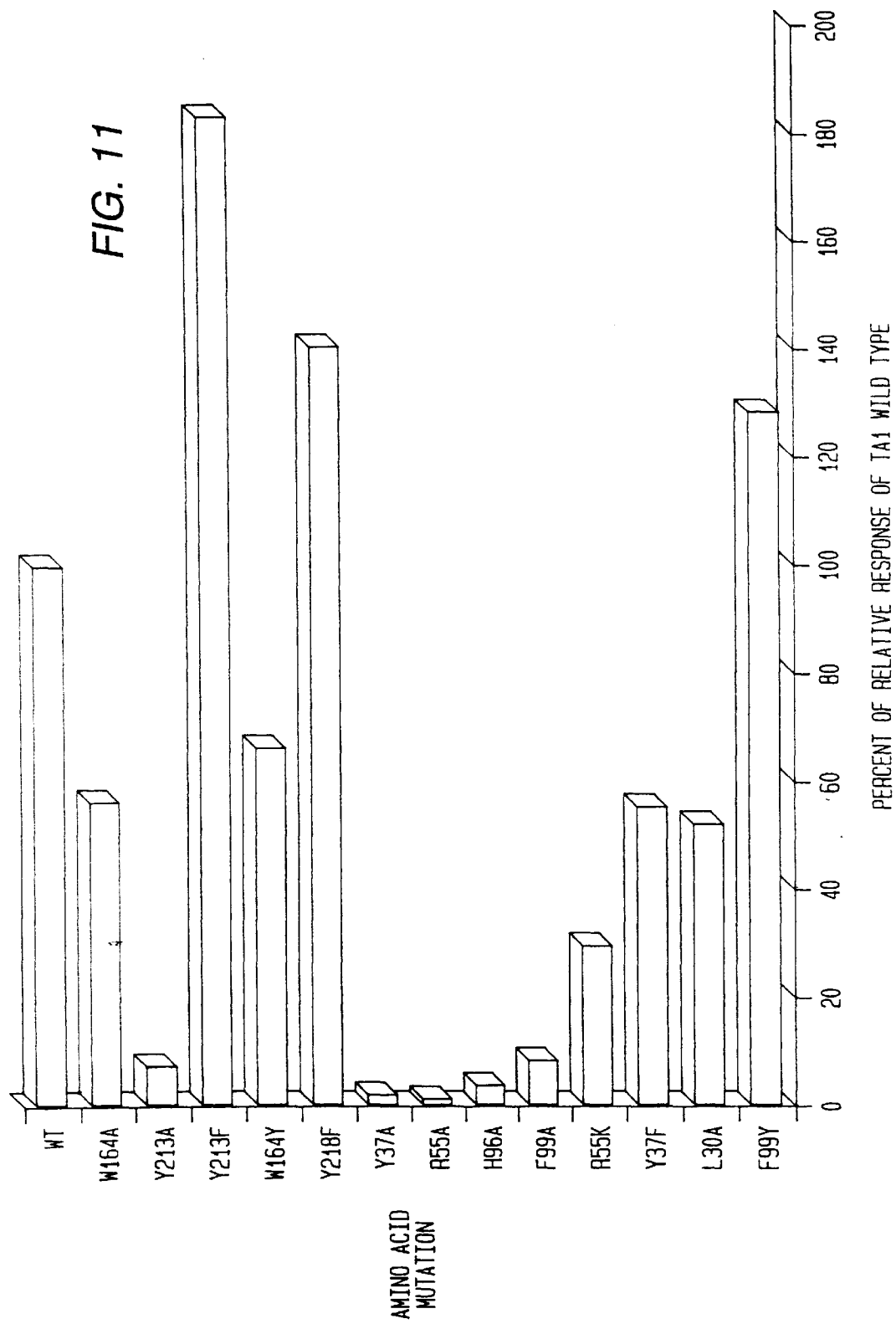

| Mutation | Sequence[a] | downstream | upstream | SEQ ID NO: |
|---|---|---|---|---|
| D1A | 5'-CCATGGGCAATCTGACCGTGACCGTGCAATCGAAGTCGAAGGATCC-3' | PKM1-1 | PKM1-2 | 1 |
| S2A | 5'-CCATGGACGCTGACCGTGCAATCGAAGTCGAAGGTCGTTGAGGATCC-3' | PKM2-1 | PKM2-2 | 2 |
| D3A | 5'-CCATGGGACTCTGCACGTGCAATCGAAGTCGTTGAGGGATCC-3' | PKM3-1 | PKM3-2 | 3 |
| R4A | 5'-CCATGGGACTCTGACGCTGCAATCGAAGTCGTTGAGGATCC-3' | PKM4-1 | PKM4-2 | 4 |
| A5S | 5'-CCATGGGACTCTGACCGTTCCATCGAAGTCGTTGAGGATCC-3' | PKM5-1 | PKM5-2 | 5 |
| I6A | 5'-CCATGGGACTCTGACCGTGCAGCTGAAGTCGTTGAGGATCC-3' | PKM6-1 | PKM6-2 | 6 |
| E7A | 5'-CCATGGGACTCTGACCGTGCTATCGCTGGTCGTTGAGGATCC-3' | PKM7-1 | PKM7-2 | 7 |
| G8A | 5'-CCATGGGACTCTGACCGTGCAATCGAAGCACGTTGAGGATCC-3' | PKM8-1 | PKM8-2 | 8 |
| R9A | 5'-CCATGGGACTCTGACCGTGCAATCGAAGTCATGAGGGATCC-3' | PKM9-1 | PKM9-2 | 9 |
| AAAAAIAGR | 5'-CCATGGGCGCTGCTGCGCCTATCGCTGGCCGTTGAGGGATCC-3' | AM001 | AM002 | 10 |
| R9K | 5'-CCATGGGACTCTGACCGTGCTATCGAAGTAAATGAGGGATCC-3' | AM003 | AM004 | 11 |
| R9I | 5'-CCATGGGACTCTGACCGTGCAATCGAAGTATCTGAGGGATCC-3' | AM005 | AM006 | 12 |
| E7Q | 5'-CCATGGGACTCTGACCGTGCTATCCAGGTCGTTGAGGATCC-3' | AM007 | AM008 | 13 |
| E7D | 5'-CCATGGGACTCTGACCGTGCTATCGACGTCGTTGAGGATCC-3' | AM009 | AM010 | 14 |
| E7K | 5'-CCATGGGACTCTGACCGTGCAATCAAAGTCGTTGAGGGATCC-3' | AM011 | AM012 | 15 |
| I6L | 5'-CCATGGGACTCTGACCGTGCACTGGAAGTCGTTGAGGATCC-3' | AM015 | AM016 | 16 |
| I6V | 5'-CCATGGGACTCTGACCGTGCAGTTGAAGTCGTTGAGGATCC-3' | AM017 | AM018 | 17 |
| A5G | 5'-CCATGGGACTCTGACCGTGGTATCGAAGTCGTTGAGGATCC-3' | AM019 | AM020 | 18 |
| A5C | 5'-CCATGGGACTCTGACCGTTGCATCGAAGTCGAAGTCGTTGAGGATCC-3' | AM021 | AM022 | 19 |
| R4K | 5'-CCATGGGACTCTGACAAAGCAATCGAAGTCGAAGTCGTTGAGGATCC-3' | AM023 | AM024 | 20 |
| D1&3N | 5'-CCATGGGAACTCTAACCGTGCAATCGAAGTCGTTGAGGATCC-3' | OP001 | OP002 | 21 |
| D1W | 5'-CCATGGTGGTCTGACCGTGCAATCGAAGTCGTTGAGGATCC-3' | OP003 | OP004 | 22 |
| S2W | 5'-CCATGGGACTGGGACCGTGCAATCGAAGTCGTTGAGGATCC-3' | OP005 | OP006 | 23 |
| D3W | 5'-CCATGGGACTCTTGGCGTGCAATCGAAGTCGTTGAGGATCC-3' | OP007 | OP008 | 24 |
| D1P | 5'-CCATGGCCGTCTGACCGTGCAATCGAAGTCGAAGTCGTTGAGGATCC-3' | OP009 | OP010 | 25 |

[a] Bases that were substituted are underlined.

Relative binding data for the PenI-C9 proteins

| Mutation | Competition EIA[a] | BIAcore[b] |
|---|---|---|
| Wild Type | 50 | 100 |
| D1A | 64 | 51 |
| S2A | 49 | 48 |
| D3A | 39 | 51 |
| R4A | 2 | 36 |
| A5S | 4 | 34 |
| I6A | 8 | 9 |
| E7A | 82 | 63 |
| G8A | 11 | 45 |
| R9A | 8 | 21 |
| AAAAAIAGR | 74 | 105 |
| R9K | 1 | 1 |
| R9I | 7 | 0.1 |
| E7Q | 88 | 96 |
| E7D | 46 | 58 |
| E7K | 94 | 113 |
| I6L | 19 | 43 |
| I6V | 19 | 64 |
| A5G | 13 | 34 |
| A5C | 27 | 7 |
| R4K | 43 | |
| D1&3N | 69 | |
| D1W | 74 | |
| S2W | 59 | |
| D3W | 44 | |
| D1P | 63 | |

[a] Reported as percent inhibition of maximum EIA signal.
[b] Reported as percent of relative response of PenI-C9 Wild Type.

Oligonucleotides used in the mutagenesis of TA1

| Mutation | Sequence of spanned region [a] | downstream | upstream | SEQ ID NO: |
|---|---|---|---|---|
| W164A | 5'-GGCCTGGAGTGGATTGGAGCGATTGATCCTGATAATGT-3' | b | CLC354 | 26 |
| Y213A | 5'-GTCTATTACTGTGACTACGCTAGTTCGACGACTATGCT-3' | b | CLC355 | 27 |
| Y37A | 5'-CATAGTAAATGGCAACACTGCCTTGTATTGGTTCCTGCAG-3' | CLC347 | CLC356 | 28 |
| R55A | 5'-CCTCAGCTCCTGATATATGCGATGTCCAACCTTGCCTCA-3' | CLC348 | CLC357 | 29 |
| H96A | 5'-GTTTATTACTGTTTTGCAGGCTCTAGAATTCCGCTCACG-3' | CLC349 | CLC358 | 30 |
| F99W | 5'-TGTTTGCAGCATCTAGAATGGCCGCTCACGTTCGGTGCT-3' | CLC350 | CLC359 | 31 |
| F99A | 5'-TGTTTGCAGCATCTAGAAGCTCCGCTCACGTTCGGTGCT-3' | CLC351 | CLC360 | 32 |
| Y213F | 5'-TGTGACTACTTCAGGTTCGAC-3' | | CLC390 | CLC391 | 33 |
| W164Y | 5'-TGGATTGGATATATTGATCTT-3' | | CLC392 | CLC393 | 34 |
| R55K | 5'-CTGATATATAGAGATGTCCAAC-3' | | CLC394 | CLC395 | 35 |
| Y37F | 5'-GGTAACACTTTCTTGTATTGG-3' | | CLC396 | CLC397 | 36 |
| L30A | 5'-AAGAGTCTCGCTCATAGTAAT-3' | | CLC398 | CLC399 | 37 |
| F99Y | 5'-CATCTAGAATATCCGCTCACG-3' | | CLC400 | CLC401 | 38 |
| Y218F | 5'-TTCGACGACTTCGCTGTGGAC-3' | | LDE001 | LDE002 | 39 |

[a] Bases that were substituted are underlined. [b] These mutations were created by site-specific mutagenesis.

CONSERVATIVE AMINO ACID REPLACEMENTS

| FOR AMINO ACID | CODE | REPLACE WITH |
|---|---|---|
| Alanine | A | D-la, Gly, β-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala |
| Isoleucine | I | D-Ile, Val, D-Val, AdaA, AdaG, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, AdaA, AdaG, cis-3,4, or 5-phenylproline |
| Proline | P | D-Pro, L-I-thioazolidine-4-carboxylic acid, D-or L-1-oxazolidine-4-carboxylic acid Kauer, U.S. Patent (4,511,390) |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |

FIG. 15B

| Tyrosine | Y | D-Tyr, Phe, D-Phe, L-Dopa, His, D-His |
|---|---|---|
| Valine | V | D-Val, Leu, D-Leu, Ile, D-Ile, Met, D-Met |

BINDING MOLECULES AND COMPUTER-BASED METHODS OF INCREASING THE BINDING AFFINITY THEREOF

BACKGROUND OF THE INVENTION

1. Field of the Invention

The present invention features novel binding molecules and methods of improving the specific binding affinity of binding molecules, which methods do not use X-ray crystallography. For example, in one aspect, the invention features methods of making antibodies with improved specific binding affinity for a polypeptide produced during prothrombin activation. The present invention is useful for a variety of applications including, e.g., producing binding molecules with improved binding affinity; and screening for binding molecules which are in low abundance.

2. Background

Proteins and polypeptides are linear polymers of amino acids that are often referred to as "amino acid residues". Naturally occurring proteins may contain as many as 20 different types of amino acid residues, each of which contains a unique side chain. The primary structure of a protein is determined by the specific sequence of amino acids in the protein.

Proteins and polypeptides generally fold into three-dimensional structures which are determined by interactions between amino acid residues. Examples of such interactions include hydrogen bonding, hydrophobic interactions, van der Waals (VDW) attraction, and electrostatic (ionic) interactions (reviewed in Stryer, L. *Biochemistry* 3rd Ed. W. H. Freeman and Co., New York (1988), pp. 15–41).

The three-dimensional structure of proteins and polypeptides can be determined in several ways. For example, X-ray crystallography has been used to analyze the structure of proteins, polypeptides, and small molecules (reviewed in Matthews, B. W., *The Proteins* 3rd Ed., (Academic Press), 3: 404–590 (1977); Van Holde, K. E. (*Prentice-Hall*, N.J.) (1971), pp. 221–239). Studies of X-ray resolved proteins and polypeptides have revealed α-helices, parallel and antiparallel β-sheets, each of which helps to determine secondary and tertiary structure (see Stryer, L., supra).

Many proteins have internal surfaces (directed away from the environment in which the protein is found) and external surfaces (which are in close proximity to the environment). Typically, hydrophobic residues such as, e.g., tryptophan, phenylalanine, tyrosine, leucine, isoleucine, valine, and methionine are found in or near the internal surface of proteins, whereas hydrophilic residues such as aspartate, asparagine, glutamate, glutamine, lysine, arginine, histidine, serine, threonine, glycine, and proline, are usually found on or near the external protein surface. Protein folding is thus dominated by the packing of hydrophobic groups into the protein interior and away from the generally aqueous solvent, thereby favorably increasing solvent entropy. The amino acids alanine, glycine, serine, and threonine are amphipathic to some extent and can be found on both internal and external protein surfaces.

X-ray crystallography has revealed binding sites (clefts) in binding molecules that form specific complexes with other binding molecules. Examples of such complexes include antibody-hapten, antibody-peptide, receptor-ligand, antibody-antibody complexes, and the complexes formed between major histocompatibility (MHC) proteins and presenting peptides (see e.g., Schulze-Gahmen, U. et al. *J. Mol. Biol.* 234: 1098 (1993); Sharon, J. *PNAS* (USA) 87:4814 (1990); Stanfield, R. L. et al. *Science* 248:716 (1990); Denzin, L. K. et al. *J. Biol. Chem.* 266:14095 (1991); Stryer, L., supra; Stern, L. J. and D. C. Wiley, *Cell* 68:465 (1992); published PCT Application No. WO 96/94314; and references cited therein). Antibody binding sites have been mutated to study models of antibody-antigen complex formation (Verdaguer, et al. *Embo. J.* 14:1670 (1995); Strong et al. *Biochem.* 30:3739 (1991)).

X-ray crystallography has also identified important amino acids called "contact residues" within the specific complexes formed between binding molecules. In general, a contact residue in a first binding molecule helps to stabilize the specific complex by forming a bond with a suitably positioned contact residue in a second binding molecule.

Although X-ray crystallography is a precise technique for detecting contact residues in binding molecules, it is often expensive and time-consuming. In some instances, it can be extremely difficult or impossible to collect crystallographic data such as, e.g., when a binding molecule fails to crystallize properly. In addition, researchers do not always have access to a facility capable of generating X-ray crystallographic data. Accordingly, it is often difficult or impossible to identify contact residues in binding molecules.

Computer-based modeling techniques for identifying contact residues in antibody-antigen or antibody-hapten complexes are known (see, e.g., Bruccoteri, R. E. et al. *Nature* 335:564 (1988); Near et al. *Mol. Immunology* 30, 4:369 (1992); Chothia, C. et al. *Nature* 342:877 (1989); Ruff-Jamison, S. and Glenney, J. R. *Prot. Eng.* 6:661 1993); del la Paz, P. et al. *Embo J.* 5, 2:415 (1986); Roberts, S. et al. *Nature* 328:731 (1987)). However, the modeling techniques have drawbacks. For example, the techniques generally use X-ray resolved antigens, or alternatively, haptens (semi-rigid structures) of known or easily predicted structure. Accordingly, the modeling techniques are often of limited value when the antigen is not a hapten, or if suitable X-ray crystallographic data is unavailable.

Antibodies which bind blood coagulation antigens are known. One blood coagulation antigen is prothrombin: a protein involved in the control of blood clotting. During blood coagulation, prothrombin is activated to thrombin; an event accompanied by the cleavage of a 271 amino acid peptide (the F1.2 peptide) from the amino terminus of prothrombin (see, e.g., Mann, K. G. et al. *Ann. Rev. Biochem.* 57:915 (1988) and references cited therein).

It would be desirable to have antibodies which specifically bind the F1.2 peptide with high affinity so that prothrombin activation can be detected in a biological sample.

It would also be desirable to have methods of identifying contact residues in binding molecules without using X-ray crystallography. Such methods would be useful in a variety of applications including, e.g., engineering binding molecules with improved binding affinity; and screening for binding molecules which are in low abundance.

SUMMARY OF THE INVENTION

The present invention features novel binding molecules and methods of improving the specific binding affinity of the binding molecules, which methods do not use X-ray crystallography. In general, the methods use binding data and interactive graphic display software programs to produce a three-dimensional model of a specific complex formed between the binding molecules. Suitably, the three-dimensional model is positioned with respect to the binding data and modeling considerations to identify contact residues in the binding molecules. The contact residues are then independently mutated to produce improved binding molecules with increased specific binding affinity. Particularly, the present invention features a method of improving the specific binding affinity of an antibody which binds a prothrombin activation fragment.

Accordingly, in one aspect, the present invention features a method of identifying contact residues in a binding site of a first binding molecule capable of forming a specific binding complex with a second binding molecule, where the method includes:

a) independently mutating one or more amino acid residues in the second binding molecule sufficient to make one or more mutated second binding molecules, b) identifying one or more amino acid residues in the second binding molecule which, when mutated as in a) above, modifies (preferably decreases) the specific binding affinity of the first binding molecule for one or more of the mutated second binding molecules, c) permitting a skilled operator to produce and view a three-dimensional model of the binding site of the first binding molecule by use of suitable interactive graphic display software programs, d) permitting the skilled operator to produce and view a three-dimensional model of the second binding molecule and to position the three-dimensional model of the second binding molecule to form a three-dimensional model of the first binding molecule and the second binding molecule in a specific binding complex, where the positioning: i) minimizes, and preferably eliminates, unacceptable steric, electrostatic and hydrophobic hinderance between the first and second binding molecules and ii) optimizes bonding between one or more amino acids in the binding site of the first binding molecule and the one or more amino acid residues in the second binding molecule identified in step b), above; and e) detecting, in the three-dimensional model of the complex, the contact residues as one or more of the amino acids in the first binding molecule which bond with one or more of the amino acid residues in the second binding molecule.

Preferably, in step b) of the above-described method, each of the mutated amino acid residues in the second binding molecule will decrease the specific binding affinity of the first binding molecule by at least 20%, more preferably by at least 50%, and most preferably by at least 95% as judged by Western blot assays disclosed below or another suitable immunological assay. Preferably, each contact residue in the first binding molecule will form one or more bonds, typically one or more hydrogen bonds, with one of the amino acid residues identified in the step b). The specific binding complex will often be rendered in a conventional "ball and stick" format.

By the term "binding molecule" is meant a protein or polypeptide capable of binding a second binding molecule to form a specific binding pair (i.e. a specific binding complex). The term further includes a molecule capable of being three-dimensionally represented in a specific binding complex without using X-ray crystallography.

The invention also provides a method of minimizing the unacceptable steric, electrostatic and hydrophobic hinderance by rendering the three-dimensional models of the first and second binding molecules in VDW surfaces, and then positioning the three-dimensional model of the second binding molecule to form a three-dimensional model of the first binding molecule and the second binding molecule in another specific binding complex. Preferably, the positioning does not allow the three-dimensional model of the second binding molecule to fully penetrating the VDW surfaces of the three-dimensional model of the first binding molecule. After formation and inspection of the specific binding complex, the three-dimensional models can be rendered in a conventional "ball and stick" format.

By not allowing the three-dimensional model of the second binding molecule to fully penetrate the VDW surfaces of the first binding molecule, the distance between each of the represented atoms does not fall below about a suitable VDW radii. Accordingly, by not allowing the full penetration, unacceptable steric, electrostatic and hydrophobic hinderance is reduced and preferably avoided.

The invention also provides a method of optimizing the bonding between the binding site of the first binding molecule and the one or more amino acid residues in the second binding molecule by:

a) determining a center of mass for each of two, four-atom pyramids formed by a main chain nitrogen, an $\alpha$-carbon, $\beta$-carbon, and a carbonyl carbon in one of the amino acids in the first binding molecule binding site and one of the amino acid residues of the second binding molecule, and examining the centers of mass, b) examining a structure comprising the eight atoms of the pyramids as a single eight atom group, c) determining a distance between the two centers of mass in the eight atom group; and d) permitting the skilled operator to manipulate the distance to form one or more bonds, typically hydrogen bonds, between the amino acid of the first binding molecule binding site and the amino acid residue of the second binding molecule.

Preferably, the distance between the two centers of mass will be below about 5Å, more preferably between about 1 Å to 4 Å. The method preferably further includes the step of determining the length of the bond and comparing the length to known bond lengths, preferably hydrogen bond lengths.

By the term "optimize" or similar term is meant that the bond between the amino acid of the first binding molecule binding site and the amino acid residue of the second binding molecule is suitably positioned to conform to acceptable bond lengths, preferably acceptable hydrogen bond lengths.

The present invention also features a method of improving the binding affinity of the first binding molecule, where the method includes mutating one or more of the contact residues in the first binding molecule to produce one or more mutated first binding molecules. The one or more mutated first binding molecules are then independently screened (by, e.g., Western blot assays which follow) to detect improved binding molecules which exhibit increased specific binding affinity for the second binding molecule.

By the term "improved" or similar term is meant that a binding molecule has been mutated in one or more contact residues to increase the specific binding affinity for another binding molecule. Generally, an improved binding molecule will exhibit at least about a 10% increase, more preferably at least about a 50% increase in specific binding affinity relative to a parental (unmutated) binding molecule, as judged by the Western blot assays disclosed below or other suitable immunological assay.

The above-described method can further include (after step e), the step of identifying contact residues in the second binding molecule. The contact residues are identified by determining which of the one or more amino acid residues in the second binding molecule forms suitable bonds with the contact residues of the first binding molecule.

Accordingly, the invention also embraces a method of improving the specific binding affinity of the second binding molecule, which method includes mutating, in the second binding molecule one or more of the contact residues identified in the second binding molecule, producing one or more mutated second binding molecules, and screening each mutated second binding molecule for improved second binding molecules. Preferably, the first binding molecule exhibits increased specific binding affinity for the improved second binding molecules.

The methods of the present invention provide a number of significant advantages. For example, the methods allow the skilled operator to identify contact residues in binding molecules without using X-ray crystallography. Accordingly, it is possible to improve the specific binding affinity of the binding molecules in a manner that is faster and less expensive than methods requiring X-ray crystallography.

Additionally, the present methods allow the skilled operator to specifically identify and target contact residues prior to mutagenesis, thereby focusing the mutagenesis to those amino acids which are responsible for specific binding between the binding molecules.

These advantages have significant benefits. For example, prior methods of mutating binding molecules (e.g., oligonucleotide-mediated mutagenesis and DNA polymerase misincorporation) are not generally capable of identifying and targeting mutagenesis to the contact residues. Accordingly, in such less suitable prior methods, the contact residues are identified by a time consuming trial and error process. Similarly, in vitro screens of cDNA or cDNA expression libraries can provide mutagenized binding molecules however, again, there is little or no identification and targeting of the contact residues, thereby making the screens generally time-intensive and difficult.

Particularly, if an improved antibody is desired, the present methods provide an efficient way of increasing specific binding affinity of the antibody without having to isolate a new (improved) antibody. In general, procedures for isolating new antibodies involve labor-intensive animal immunizations and serum testing (sometimes spanning 6 months or more), with no guarantee that the new antibody will ever be obtained. However, in accordance with the present methods, improved antibodies are obtained without immunizations and serum testing because the antibodies are designed by mutating contact residues in an existing parental antibody.

In general, improved binding molecules are useful in a variety of applications including in vitro screens for detecting binding molecules which specifically bind the improved binding molecules. For example, a peptide which binds an antibody with low affinity is more readily detectable with an improved antibody of the invention than with the parental antibody. Additionally, a peptide which is in low abundance, e.g., as in a library of peptides or a biological sample, is more readily detectable with an improved antibody of the invention. More specifically, improved antibodies of the invention are particularly useful in diagnostic and research settings such as in vitro diagnostic imaging and in situ detection of epitopes in tissue.

Additionally, improved antigens have a number of uses and advantages, including the detection of antibodies in low abundance or which bind antigen with low binding affinity. For example, improved antigens are especially useful in laboratory screens of polyclonal and monoclonal antibodies, which antibodies can often weakly bind parental antigen. Further, screens of cDNA and phage display libraries expressing antigen-binding antibody fragments are more efficiently conducted with an improved antigen of the invention. Additionally, the improved antigens can be used to detect weakly binding antibodies by a number of suitable immunological techniques, such as RIA. Still further, the improved antigens can be used to purify antibodies by immunoaffinity chromotography, particularly antibodies which weakly bind the parental antigen. Moreover, improved antigens are useful as therapeutic agents which either alone, in combination with other agents, or in modified form (e.g., chemically modified to improve circulating half-life), can reduce the severity of an undesirable immune reaction (e.g. an autoimmune disease or allergy) by inhibiting binding of deleterious antibodies.

In another aspect of the present invention there is provided an antibody which includes the TA1 $V_L$ region (FIG. 1 SEQ ID NO. 41) and $V_H$ region (FIG. 2 SEQ ID NO. 43), which regions are capable of specifically binding the F1.2 fragment of prothrombin. The TA1 antibody and improved TA1 antibodies are are useful in a variety of applications including, e.g,. detection of prothrombin activation in a sample from a patient suffering from (or suspected of having) a blood coagulation disorder such as disseminated intravascular coagulation or exercise-induced angina. In addition, the TA1 antibody is particularly useful as a control for screening improved antibodies with increased F1.2 fragment binding affinity. Suitably, the TA1 antibody and improved TA1 antibodies of the invention or F1.2-binding fragments thereof can be provided as a kit for detecting prothrombin activation in a biological sample.

In another aspect of the present invention, there is provided an isolated DNA which includes a DNA sequence encoding a $V_L$ region of an antibody light chain with at least 80% homology to the amino acid sequence shown in FIG. 1 (SEQ ID NO. 41) and which is capable of specifically forming an F1.2 binding domain with the TA1 $V_H$ region shown in FIG. 2 (SEQ ID NO: 43). Additionally, the invention also provides an isolated DNA which includes a DNA sequence encoding a $V_H$ chain of an antibody heavy chain with at least 80% homology to the amino acid sequence of the TA1 $V_H$ chain shown in FIG. 2 (SEQ ID NO: 43), which $V_H$ chain is capable of specifically forming an F1.2 binding domain with the TA1 $V_L$ chain shown in FIG. 1 (SEQ ID NO. 41). Preferably, each homology is at least 80%, more preferably at least 90%, even more preferably at least 99% with respect to the TA1 $V_L$ and $V_H$ chains, respectively. Still more preferably, the isolated DNA comprises a DNA sequence encoding a polypeptide consisting of the TA1 light chain of FIG. 1 (SEQ ID NO. 41) or the TA1 heavy chain of FIG. 2 (SEQ ID NO. 43).

Further provided are isolated DNAs capable of hybridizing to a DNA sequence encoding either the TA1 $V_L$ chain of FIG. 1 (SEQ ID NO. 40) or the TA1 $V_H$ chain OF FIG. 2 (SEQ ID NO. 41) under high stringency hybridization conditions. Preferably, the isolated DNAs are at least 300 nucleotides in length and encode a polypeptide capable of forming an F1.2 binding domain with either of the TA1 $V_L$ chain of FIG. 1 (SEQ ID NO 41) or the TA1 $V_H$ chain of FIG. 2 (SEQ ID NO. 43). More preferably, the isolated DNAs are between about 300 to 400 nucleotides in length.

The present invention also provides vectors which include an isolated DNA operatively linked to DNA sequences encoding a suitable immunoglobin constant chain, which chain allows the isolated DNA to be expressed as a full-length antibody capable of specifically binding the F1.2 polypeptide (or F1.2 binding fragment of a full-length antibody).

Accordingly, the invention also embraces cells which include an isolated DNA of the invention, as well as a vector which includes the isolated DNA. Generally, the cells are capable of replicating the vectors. Alternatively, (or in addition), the cells are capable of expressing the isolated DNAs in the cell or in the cell culture medium under suitable cell culture conditions. The invention also includes substantially pure TA1 antibody and improved TA1 antibodies (or fragments thereof) made by suitably co-expressing the vectors in cells, and then purifying the antibodies by contacting the cell (preferably a cell lysate) or the cell culture medium with the prothrombin F1.2 fragment (or a TA1-binding fragment thereof) under conditions which specifically bind the antibodies and the prothrombin fragment. Preferably, the substantially pure antibodies or fragments thereof are purified in accordance with standard immunoaffinity chromotography techniques and are capable of specifically binding the F1.2 fragment.

BRIEF DESCRIPTION OF THE DRAWINGS

Still other features, advantages and aspects of the present invention will become apparent from the description of illustrative embodiments hereinafter, when read in conjunction with the drawings of which:

FIG. 1 shows the nucleotide (SEQ ID NO: 40) and amino acid sequence (SEQ ID NO: 41:) of the TA1 antibody $V_L$ chain, including sites of hydrogen bond interactions (shaded boxes). Also depicted are mutations which improved specific binding affinity (light box) or which were made to produce control antibodies (see text). L1, L2 and L3 refer to variable chain loops. Eco RV and Eag I refer to restriction enzyme cleavage sites.

FIG. 2 shows the nucleotide (SEQ ID NO: 42) and amino acid sequence (SEQ ID NO: 43) of the TA1 antibody $V_H$ chain, including sites of hydrogen bond interactions (shaded boxes). Also shown are mutations which improved specific binding affinity. H1, H2 and H3 refer to complementarily determining loops. Eco RV and Eag I refer to restriction enzyme cleavage sites. Amino Acid position 1 of SEQ ID NO: 43 corresponds to amino acid 114 in the TA1 heavy chain.

In FIG. 3A, HC $F_v$ refers to the heavy chain DNA sequence depicted in FIG. 2. LC $F_v$ in FIG. 3B refers to the light chain DNA sequence depicted in FIG. 1. The diagrams show the location of various restriction enzyme cleavage sites, selectable markers; as well as promoter, enhancer and leader sequences. Abbreviations: gpt, geneticin (G418) resistance gene; Neo, neomycin resistance gene.

FIG. 4A is a coomassie blue stained gel. Text along the top portion of each photograph refers to specific C9 mutations. "WT" refers to parental C9 antigen (unmutated).

Figure 3A:
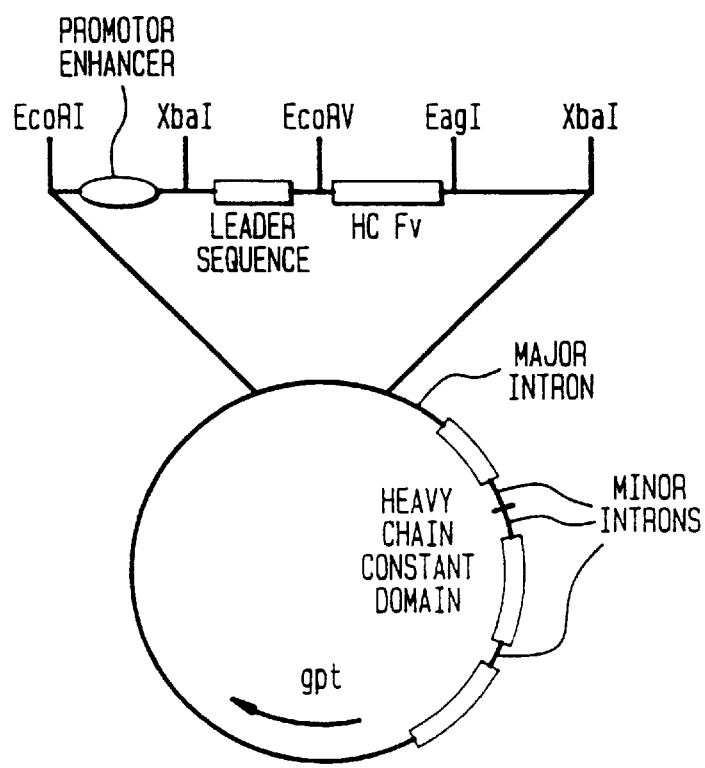
FIGS. 3A and 3B are schematic diagrams of DNA vectors used to make the TA1 antibody and improved TA1 antibodies.

FIG. 4B is a Western blot probed with detectably labelled TA1 antibody. In both gels, about 1 μg of protein was added to each lane.

FIG. 5 is a photograph of a three-dimensional model of the TA1 antibody binding site (no bound C9 antigen).

FIG. 6 is a photograph of a three-dimensional model of an initial TA1-C9 complex.

FIGS. 7A–7F are photographs of three-dimensional models of the initial TA1-C9 complex after refinement.

FIG. 7A shows the C9 antigen and TA1 antibody binding site as a space filled rendering. Shown are the α-carbon backbone and sidechains of the antigen and framework regions, light chain and heavy chain CDR regions of the TA1 antibody.

FIG. 7B depicts the C9 antigen α-carbon backbone as a ribbon and sidechain in ball and stick form. The TA1 binding site is a space filled rendering with the framework regions removed for the sake of clarity.

FIG. 7C is a ball and stick rendering of two specific hydrogen bonds which occur between the TA1 antibody binding site and the C9 antigen. One hydrogen bond (length about 1.12A) is shown between Arg55 in TA1 L2 and an amine group in the Arg#9 sidechain. A second hydrogen bond (length about 2.45 Å) is depicted between Tyr37 in TA1 (L1) and the amide group in the Arg#9 sidechain.

FIG. 7D is a ball and stick rendering of a hydrogen bond (length of about 1.36 Å) between Trp164 in the TA1 binding site (H2 loop) and the backbone amine at Ala#5 in the C9 antigen.

FIG. 7E is a ball and stick rendering of a hydrogen bond (length of about 1.71 Å) occurring between His96 in the TA1 binding site (L3 loop) and Arg#4 sidechain in the C9 antigen.

FIG. 7F is a space filling rendering of the TA1 binding site with mutated amino acid residues (see text) and a ball and stick rendering of the C9 antigen.

FIGS. 8A and 8B are Ramachandran plots of the three-dimensional model of the TA1 binding site (8A) and the initial TA1-C9 complex model (8B).

FIGS. 9A and 9B are photographs of SDS-PAGE gels showing various PenI-C9 fusion proteins.

FIG. 9A is a coomassie blue stained gel. Text along the top portion of each photograph refers to specific C9 mutations.

FIG. 9B is a Western blot probed with labelled TA1 antibody. In both gels, about 1 μg of protein was added to each lane.

FIGS. 10A and 10B are photographs of SDS-PAGE gels showing various PenI-C9 fusion proteins.

FIG. 10A is a coomassie blue stained gel. Text along the top portion of each photograph refers to specific C9 mutations.

FIG. 10B is a Western blot probed with labelled TA1 antibody. In both gels, about lug of protein was added to each lane.

FIG. 11 is a graph showing the specific binding affinity of mutated TA1 antibodies for penI-C9 fusions relative to the parental TA1 antibody (100% binding). "WT" signifies a PENI-C9 fusion with parental C9 antigen. Amino acid positions 164, 213 and 218 correspond to amino acid positions 50, 99, and 104, respectively, in FIG. 2 (SEQ ID NO: 43).

FIG. 12 is a table showing oligonucleotides used for the mutagenesis of the C9 antigen.

FIG. 13 is a table showing binding data for PenI-C9 fusion proteins.

FIG. 14 is a table illustrating the oligonucleotides used for the mutagenesis of TA1 antibody.

FIGS. 15A and 15B are tables showing conservative amino acid replacements.

DETAILED DESCRIPTION OF THE INVENTION

In general, we have discovered methods of improving the specific binding affinity of binding molecules, which methods do not require the use of X-ray crystallography. In accordance with the methods, the skilled operator can identify contact residues in a first binding molecule by suitably positioning a three-dimensional model of a first binding molecule and a second binding molecule to form a three-dimensional model of a specific binding complex. Once the contact residues are identified, they are independently mutated (e.g., with a pre-selected amino acid such as alanine, serine or tryptophan) to produce mutated first binding molecules. By independently screening each mutated first binding molecule for those exhibiting increased specific binding affinity for the second binding molecule, improved first binding molecules are obtained. The present methods can also be used to identify contact residues in the second binding molecule so that improved antigens can be obtained.

The preparation of TA1 antibody, improved TA1 antibodies, C9 antigen, and improved C9 antigens was accomplished in accordance with the present methods and standard laboratory techniques. Although the following discussion is with specific reference to the production of TA1 antibody, improved TA1 antibodies, C9 antigen, and improved C9 antigens, it will be appreciated that other binding molecules can be suitably improved in accordance with the present methods, except where specifically noted.

The TA1 antibody, like other antibodies, is a four chain structure (2H+2L) that includes a variable $F_v$ domain, which domain consists of a $V_L$ (variable light chain) and $V_H$ (variable heavy chain) region. The $V_L$ and $V_H$ regions include six packed interstrand loops (i.e. complimentarily determining regions or "CDRs"): three derived from the variable heavy chain (H1, H2, and H3) and three from the variable light chain (L1, L2, and L3). The L1, L2, H1 and H2 loops are each encoded by $V_L$ and $V_H$ genes, whereas the L3 and H3 loops are encoded by the V gene junctions and their respective modifying gene segments. Framework (FR) regions (4 FR in both heavy and light chains) flank the 3 CDR regions within hypervariable regions of both heavy and light chains (i.e. FR1, CDR1, FR2, CDR2, FR3, CDR3, FR4). See also Searle, S. J. et al. *Antibody Engineering* 2nd Ed. (Oxford University Press, NY) pp. 3–51 (1995).

In general, to perform the present methods, it is necessary to select binding molecules for which an improvement in specific binding affinity is desired. For example, if improvement in the specific binding affinity of an antibody and antigen is desired, it is necessary to know the DNA and amino acid sequence of the antibody, typically from the N-terminus of the heavy and light chains up to at least about framework region 4 (FR4). With respect to the antigen, it is necessary to know the DNA and amino acid sequence of the antigen, preferably that portion of the antigen which is specifically bound by the antibody (i.e. the portion including an immunologically recognizable epitope). Exemplary antigens are polypeptide fragments bearing immunologically-recognizable epitopes derived from blood coagulation proteins such as the F1.2 peptide, preferably the C9 peptide disclosed herein; polypeptide hormones, cytokines, viral coat proteins, and cell surface proteins such as MHC molecules (class I and II). Preferably, the antigen has a length of between about 2 to 15 amino acids, more preferably between about 5 to 10 amino acids, and most preferably about 10 amino acids in length.

The antibody can be full-length, or alternatively, the antibody can be an immunoglobin fragment capable of specifically binding the antigen. Exemplary antibody fragments include, e.g., $F_v$, $Fab^1$ and $F(ab^1)_2$ fragments, "half-molecules" derived by reducing the disulfide bonds of immunoglobins, single-chain immunoglobins or other suitable antigen-binding fragments (see e.g., Bird et al. Science 242, 424 (1988); Huston et al. PNAS (USA) 85, 5879 (1988); Webber et al. Mol. Immunol. 32, 249 (1995)). The antibody or antigen-binding portion thereof may be of animal (e.g., a rodent such as a mouse or rat), or human origin, or it may be chimeric or humanized (see e.g., Morrison et al., PNAS 81, 6851 (1984); Jones et al. Nature 321, 522 (1986)). Preferred antibody fragments are those capable of binding the prothrombin F1.2 polypeptide as judged by Westen blot experiments described herein.

The DNA and amino acid sequences of binding molecules can be obtained from a wide variety sources. For example, about 2000 immunoglobin variable region DNA and amino acid sequences are publicly available through the Brookhaven Protein Data Bank (BPDB) (Brookhaven Protein Data Base, Chemistry Dept. Brookhaven National Laboratory, Upton, N.Y. (1973); see e.g., Searle, S. J. et al. supra) and other databases such as Genbank. Of course, if a particular database only provides the DNA sequence of an immunoglobin variable region of interest, it can be conceptually translated into the corresponding amino acid sequence in accordance with the genetic code (see e.g., Stryer, L. supra). Similarly, DNA and amino acid sequences of a variety of antigens are available from these and other public databases.

More specifically, to prepare improved TA1 antibodies and improved C9 antigens, a three-dimensional model of the TA1 antibody binding site (i.e. essentially comprising the $V_H$ and $V_L$ domains) was made by using a minicomputer integrated with suitable interactive display graphic software. The interactive display graphic software preferably combined, in a single program, energy screening, canonical structure residue searches, and a Monte Carlo System. A preferred software package was the ABM™ system of Rees, A. R. et al. (Rees et. al., ABM™, a computer program; Oxford, U.K.: *Oxford Molecular Ltd.* 1992, Martin et. al., *Proc. Natl. Acad. Sci.* 86:9268–9272 1989). A suitable general modeling program preferably included a suitable solvation software package for visualizing water molecules in and around the TA1 binding site. Especially preferred general modeling programs included the Insight II (Biosym) or Sybyl (Tripos Associates) software systems, or comparable software offered by Molecular Simulations.

Generally, the software packages were integrated with a suitable mini-computer CPU system which included a display terminal with resident three-dimensional application software (see below) and associated input and output devices, such as X-Y plotters, keyboard and position control devices (e.g., potentiometers, an X-Y tablet, or a mouse). For example, one suitable hardware system was the silicon graphics Indigo Z Extreme system. Memory and CPU requirements were typically variable, so memory expansion units of up to about 20 gigabytes were included in the hardware system. Memory and CPU capacity in this range were found to be greater than that necessary to perform the methods of the present invention. Other suitable hardware systems are available from Hewlett-Packard.

Figure 5:
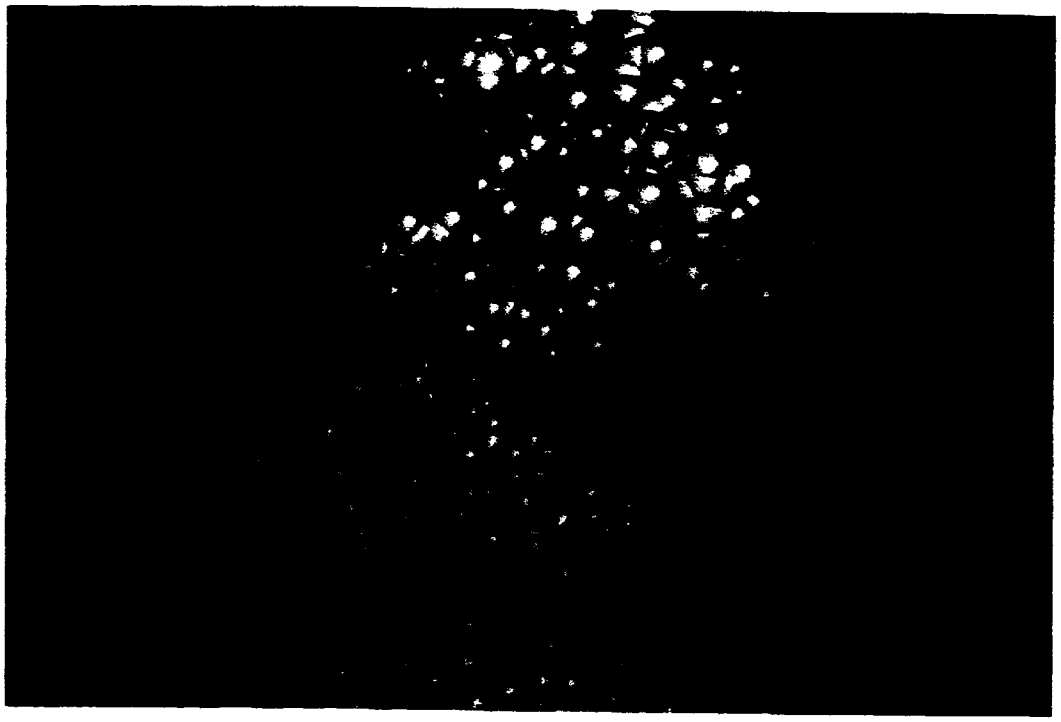

The amino acid sequence of the TA1 binding site (i.e. N-terminus of each heavy and light chain region to about FR4) was integrated with the interactive display graphic software to make the three-dimensional model of the TA1 binding site. By inspection of the model, amino acid residues which generally constrained and restrained the binding site were observed. The modeling of the TA1 binding site is disclosed in Example 2 and a photograph of the three-dimensional model of the TA1 binding site is shown in FIG. 5 which follows.

In general, it was important that the volume inside the three-dimensional model of the complex be nearly filled with hydrophobic residues and that polar or charged (hydrophilic) amino acid residues make suitable hydrogen bonds with each other or with the solvent water. Accordingly, an unacceptable hydrophobic hindrance also occurred when, in the three-dimensional model of the TA1 binding site, a hydrophobic residue was in contact with solvent or was between about 1 Å–5 Å from a polar or charged amino acid residue.

In parallel experiments, each amino acid residue of the C9 antigen was independently mutated by conventional recombinant mutagenesis techniques starting at about the N-terminus of the antigen and progressing consecutively to the C-terminus. In the examples which follow, alanine was often used to mutagenize the C9 antigen by alanine scanning mutagenesis (see generally Sambrook et al. supra; Ausubel et al. *Current Protocols in Molecular Biology*, Green Publishing Associates and Wiley *Intersciences* (1993); Kunkel, *PNAS* (USA) 82, 488–492 (1985); Nisbet I. T. et al., *Gene Anal. Tech.* 2, 23–29 (1985); and Hines, J. C., et al., *Gene*, 11, 207–218 (1980)). In general, scanning mutagenesis of the C9 antigen was used to produce P mutated C9 antigens, where P was the total number of amino acids in the antigen (nine). By the term "mutated" as it is used herein with reference to an antigen (or other molecule) made in accordance with the present methods, is meant a binding molecule which differs in at least one amino acid from a corresponding parent molecule.

Figure 4A:
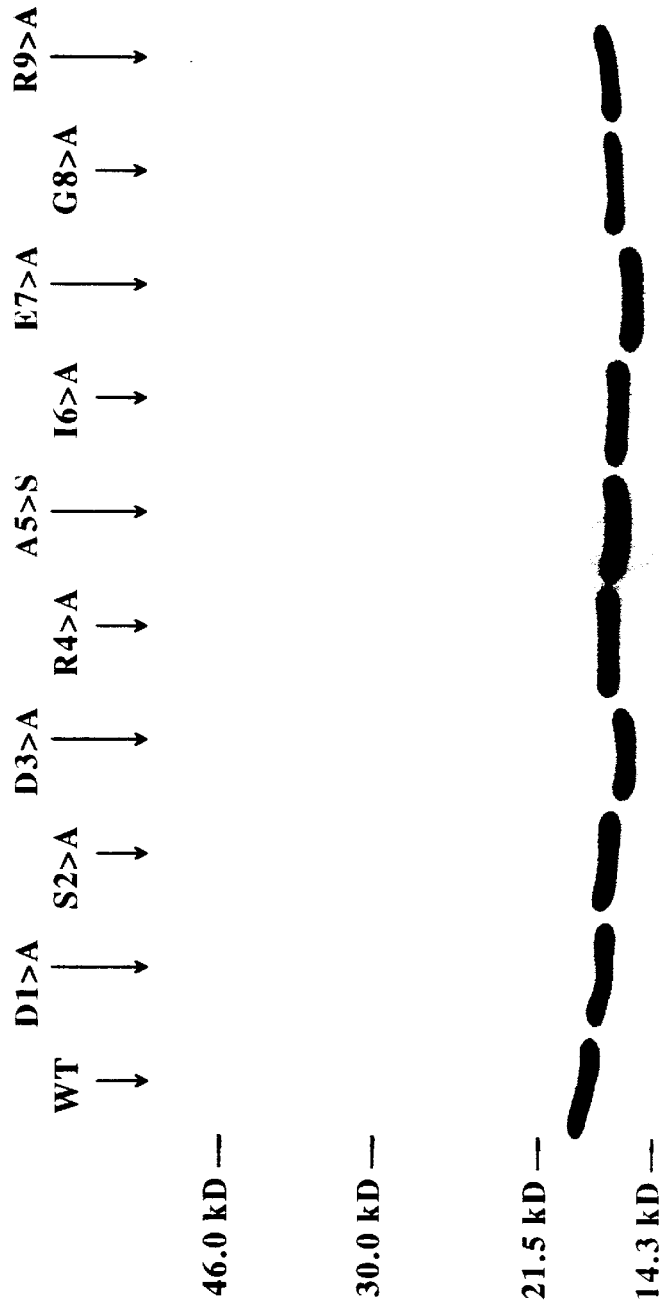
FIGS. 4A and 4B are photographs of SDS-PAGE gels showing various PenI-C9 fusion proteins.
Figure 4B:
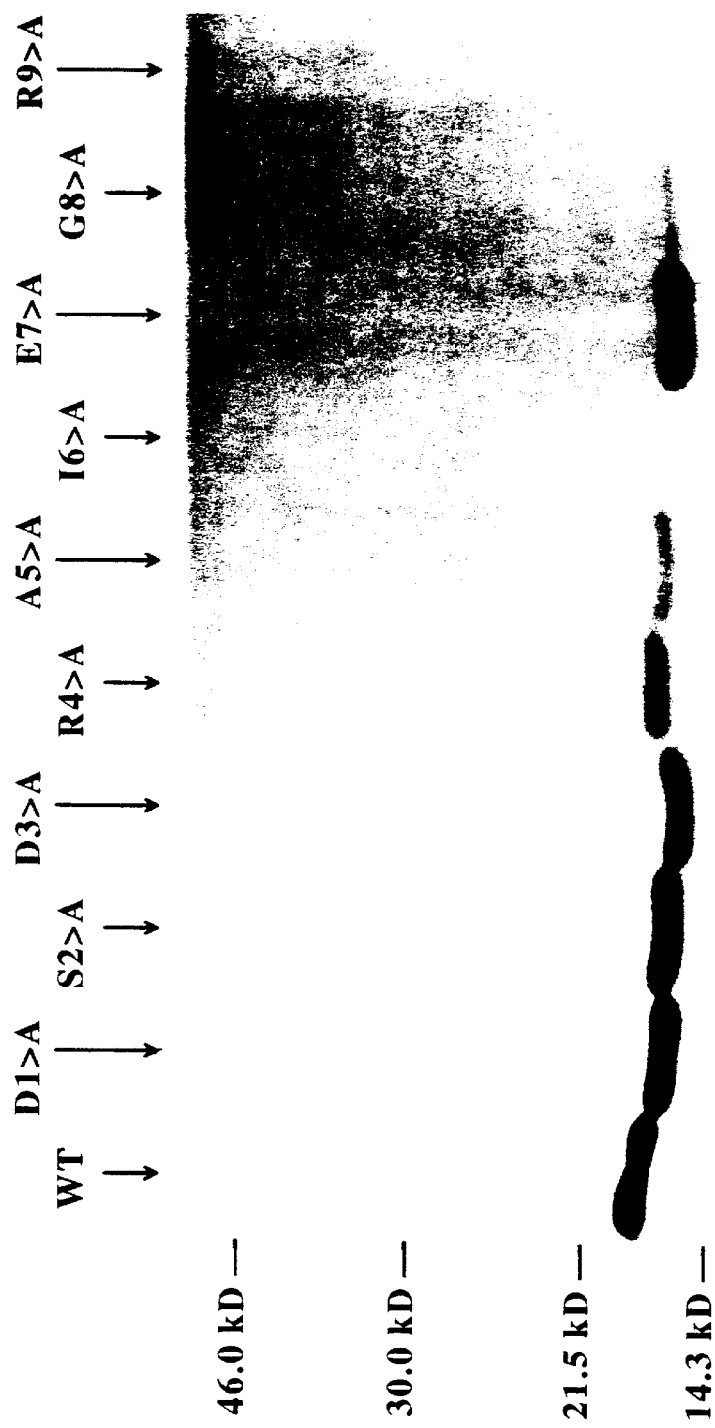
Figure 9A:
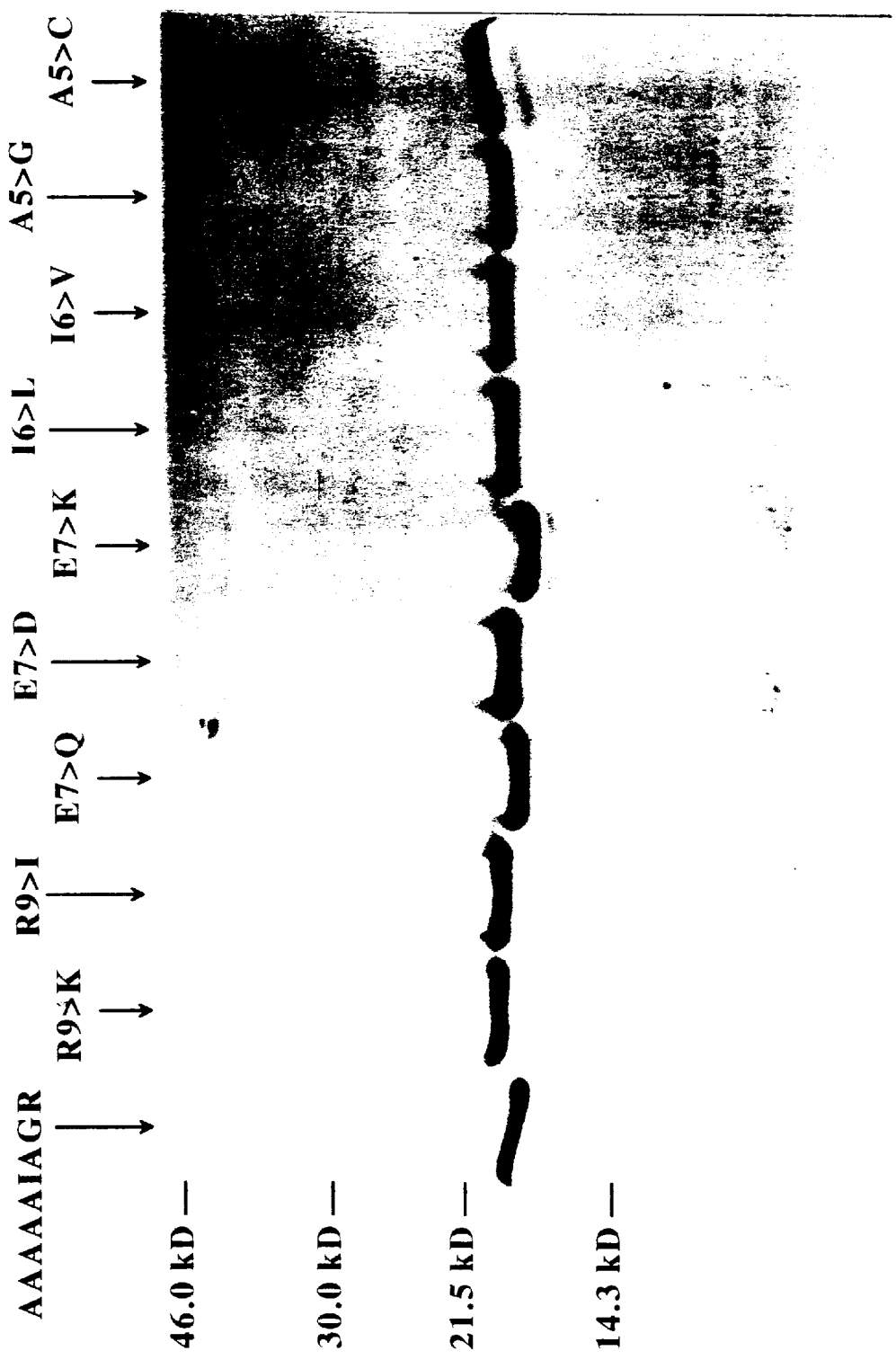
Figure 9B:
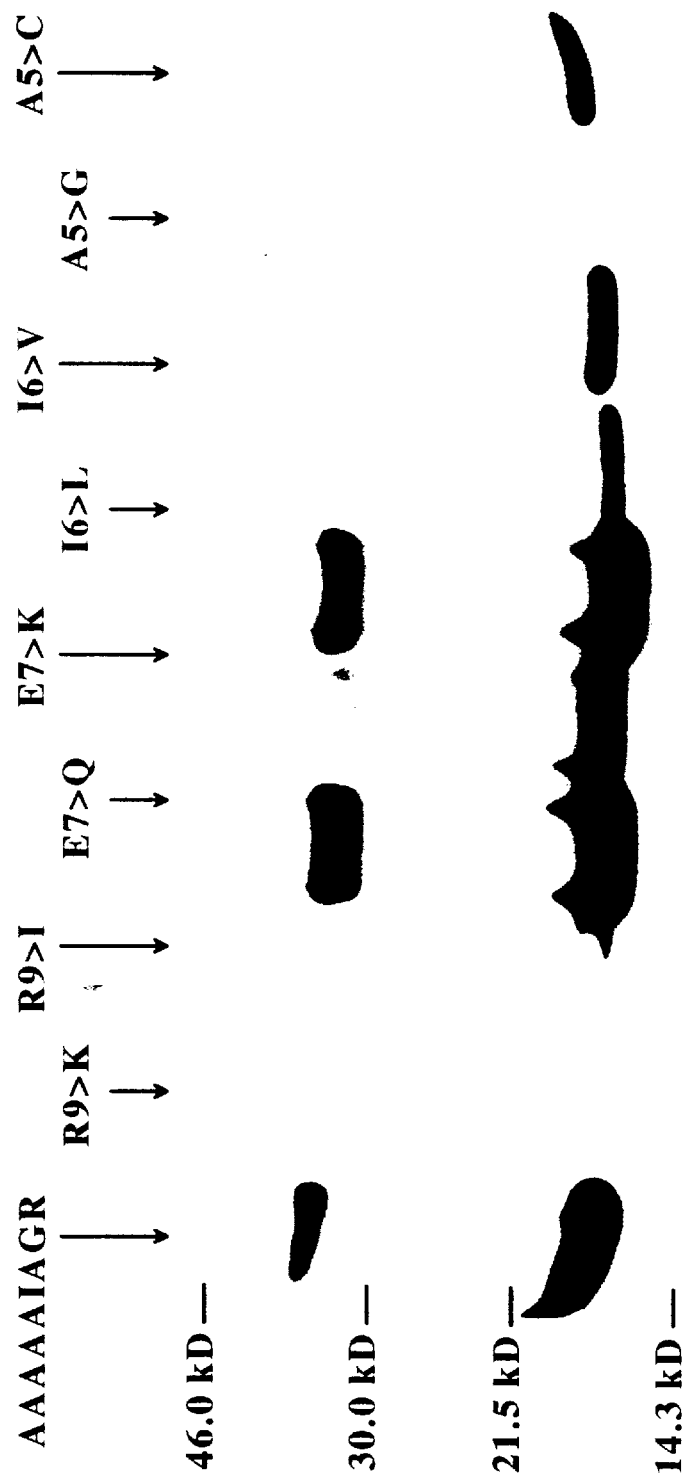
Figure 10A:
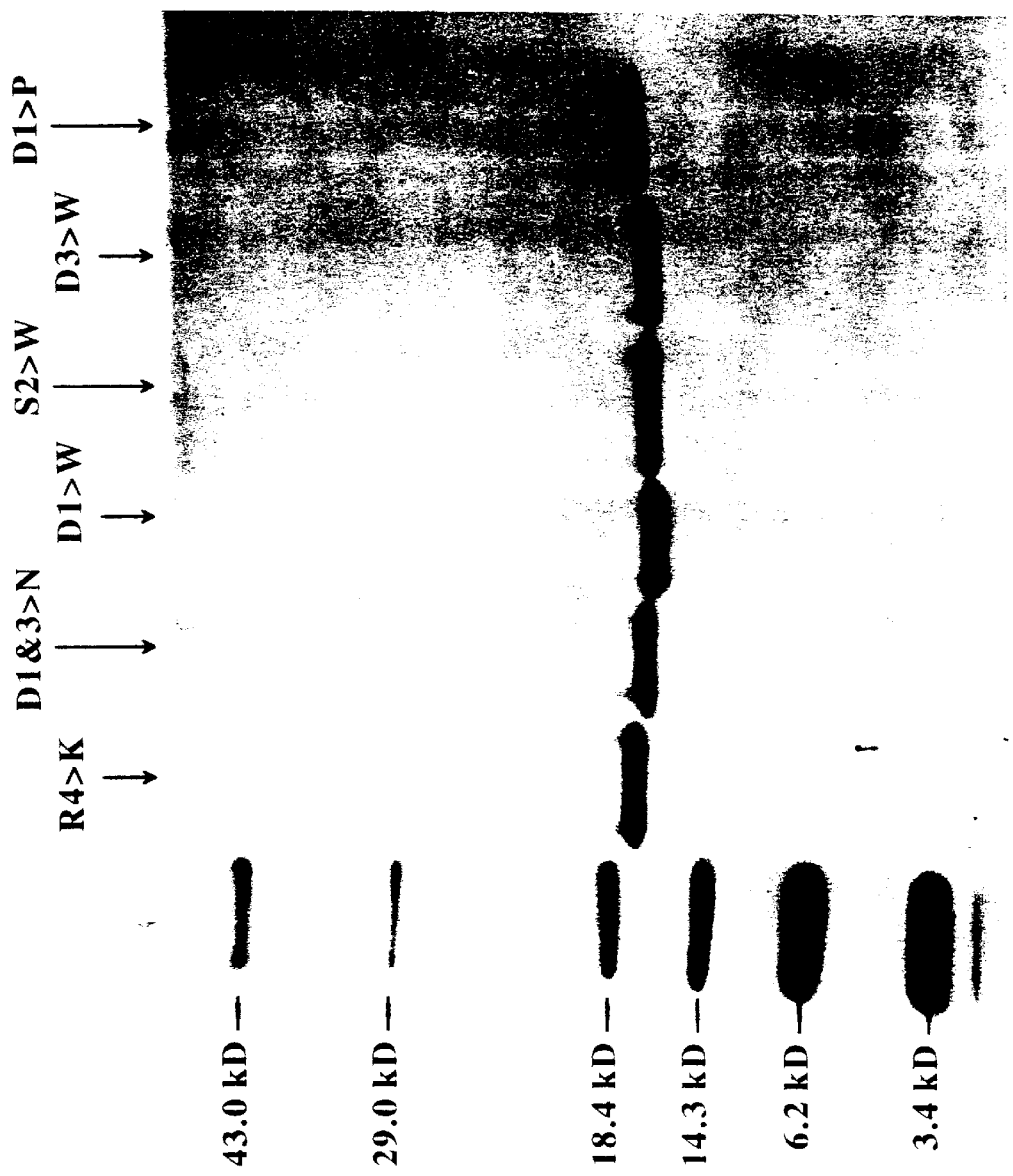
Figure 10B:
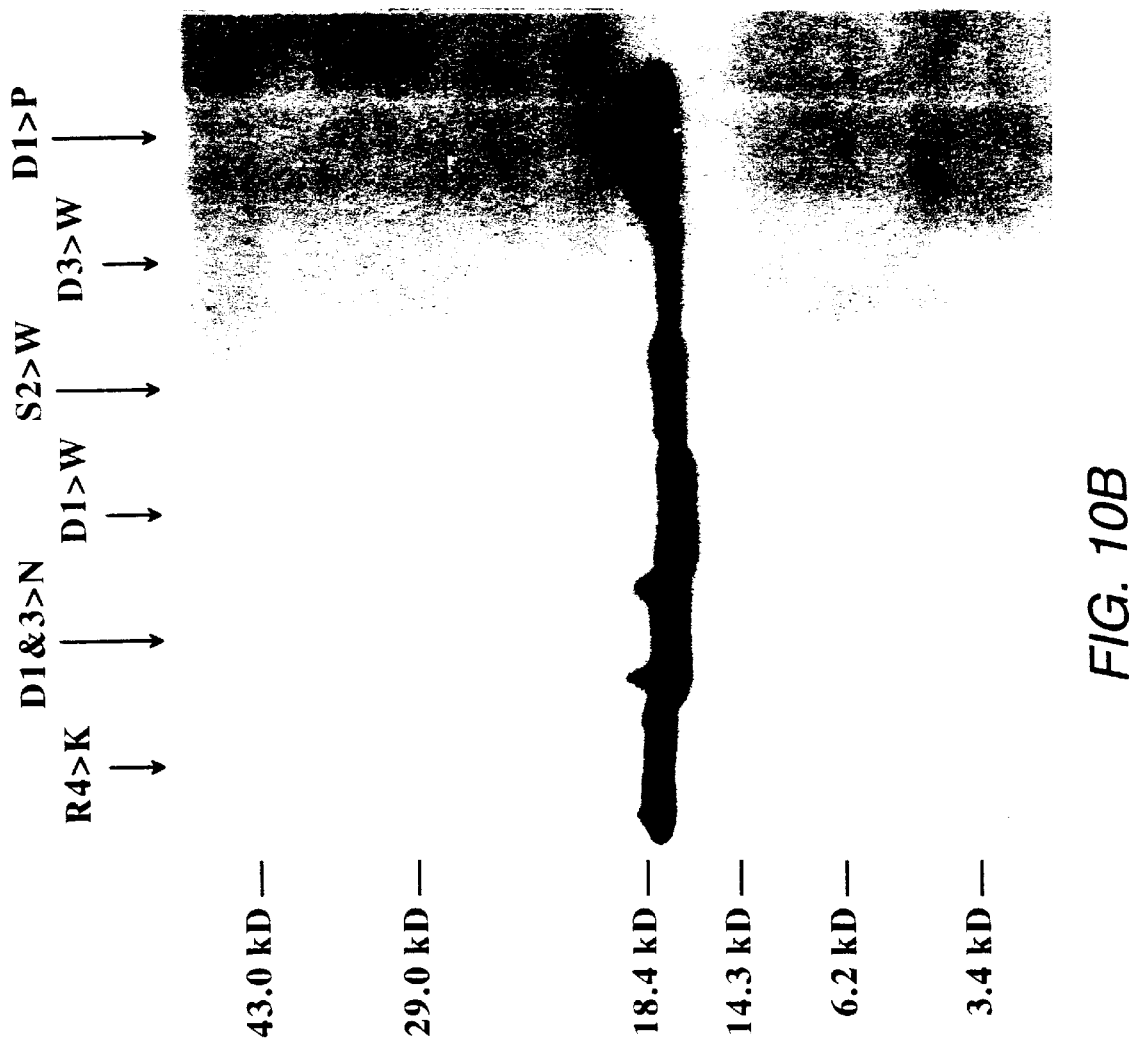

The specific binding affinity of each mutated C9 antigen was then experimentally determined by Western blot assay (see FIGS. 4B, 9B, 10B which follow). Amino acid residues in the C9 antigen, which when mutated, substantially decreased binding with the TA1 antibody were operationally defined as "candidate antigen contact residues". As will be discussed more fully below, whether or not the candidate antigen contact residues were contact residues required inspecting a three-dimensional model of the TA1 antibody bound to the C9 antigen. Generally, the candidate antigen contact residues decreased the specific binding affinity of the TA1 antibody by at least 20%, more preferably at least 50%, most preferably at least 95% with respect to the binding of the parental C9 antigen to the TA1 antibody. Specific binding affinity was determined by the Western blot assays described below.

The three-dimensional model of the TA1 binding site was energy minimized by use of a suitable general modeling program such as the Insight II software program. Suitably, another general modeling program such as the Insight II Builder Module was used to produce, view, and position a three-dimensional model of the C9 antigen to form a three-dimensional model of the specific binding complex formed between the TA1 antibody and the C9 antigen. Suitable positioning of the C9 antigen model with respect to the TA1 binding site model was guided by minimizing unacceptable steric, electrostatic and hydrophobic hinderance (i.e. modeling considerations) and optimizing specific binding interactions between the candidate C9 contact residues and suitably positioned amino acid residues in the TA1 binding site. In general, the specific binding interactions were preferably optimized with respect to the candidate C9 contact residues.

For example, mutation of an arginine at position 9 of the C9 antigen nearly eliminated TA1 binding (see FIG. 9B). Accordingly, the specific binding interactions between the C9 antigen and the TA1 binding site were optimized with respect to the arginine (and other candidate C9 contact residues). The construction and purification of C9 mutants, modeling of a TA1-C9 complex, and detection of contact residues is disclosed in Examples 3–5, which follow.

By the term "positioning" is meant suitably changing the dihedral angles of the three-dimensional model of the second binding molecule, or directionally rotating or translating the three-dimensional model of the second binding molecule, so as to form the three-dimensional model of the specific binding complex. The term is further meant to mean that acceptable dihedral angle movements are typically 360 degrees around the axis of bond rotation between any two bonded atoms of a second binding molecule such as the C9 antigen. More specifically, rotational and translational movements were achieved by rotating and suitably placing the entire C9 peptide anywhere on the x, y, z, axis, e.g. placement along the x, y, z axis within the TA1 binding cleft.

The suitable positioning of the C9 antigen model with respect to the TA1 binding site model was performed by rendering the C9 antigen model in a conventional "ball and stick" format and the TA1 binding site model in VDW surfaces. Accordingly, when the C9 antigen model was suitably positioned in the model of the TA1 binding site, it was possible to minimize unacceptable steric, electrostatic, and hydrophobic hindrance, while optimizing specific binding between the candidate C9 contact residues and the suitably positioned amino acids in the TA1 binding site model. As will be readily apparent, it is also possible to render both models in ball and stick format while optimizing the binding between the C9 antigen and the TA1 binding site, provided that the TA1 binding site, and optionally the C9 antigen, is rendered in VDW surfaces to verify that the binding does not lead to unacceptable steric, electrostatic, or hydrophobic hinderence.

The step of optimizing specific binding between the candidate C9 contact residues and suitably positioned amino acid residues in the TA1 binding site required determining the distance between two centers-of-mass of a suitably positioned amino acid in the TA1 binding site and a candidate C9 contact residue. If the distance was not optimal for making one or more suitable bonds, typically one or more hydrogen bonds, the distance was manipulated, so long as unacceptable steric, electrostatic and hydrophobic hinderance was minimized. If the distance fell within an acceptable bond distance, and the unacceptable hinderance was minimized (or preferably absent), the distance between the two centers of mass was "locked in" and another pair of amino acids was considered. Generally, the distance separating the "locked in" residues was between about 1 Å to 5 Å, preferably between about 1 Å to 4 Å and most preferably about 2 Å.

The "locked in" distance between the two centers of mass thus separated two contact residues: one in the TA1 binding site and the other in the C9 antigen. Accordingly, a "suitably positioned" amino acid in the TA1 binding site was an amino acid which was generally separated from a candidate C9 contact residue by between about 1 Å to 5 Å, preferably between about 1 Å to 4 Å, and most preferably about 2 Å.

It is understood that hydrogen bonds can form between various portions of amino acids in binding molecules such as between amino acid side chains, between amino acid side chains and suitable atoms of the polypeptide backbone (e.g., the carbonyl oxygen), and between amino acid side chains. Hydrogen bond lengths are known; generally they are between about 1 Å–5 Å. A compilation of hydrogen bond distances has been reported by Stryer, L., supra (Table 1-1, pg. 7, fully incorporated herein by reference). Hydrogen bonds can also form between the various portions of amino acids and a water molecule held within a first binding molecule such as an antibody. Accordingly, a contact residue in a second binding molecule such as an antigen can bind with the water molecule. Such binding can be detected with general modeling programs (e.g., Insight) which include solvation packages.

To refine and confirm the three-dimensional model of the specific TA1-C9 binding complex and to produce improved TA1 antibodies, each TA1 contact site (in the TA1 variable region) was recombinantly mutagenized. In general, for each antibody contact residue identified in the three-dimensional model of the complex, Q number of individually mutated TA1 variable region genes was produced, where Q represents the total number of TA1 antibody contact residues detected by the present method.

TA1 antibodies carrying individually mutated contact residues (i.e., in one of the TA1 variable regions) were produced and then tested for improved specific binding affinity with the C9 antigen. Binding data derived from the tests was then used to refine the three-dimensional model of the complex. By the term "refine" or similar term is meant that the three-dimensional model of the complex was manipulated to optimize suitable bonding, preferably hydrogen bonding, between all the contact residues in the TA1 antibody and C9 antigen. For example, the refinement of an initial TA1-C9 complex model and preparation and testing of mutated TA1 antibodies is disclosed in Examples 6 and 7 which follow.

By the term "specific binding" or similar term is meant a binding molecule (e.g., an antibody) which binds another molecule (e.g., an antigen) to form a specific binding complex, but which does not recognize and bind unrelated molecules as determined by, e.g., Western blot as disclosed herein or other acceptable binding assays such as gel mobility shift assay, or ELISA. See also Sambrook et al. infra, and Ausubel et al. infra. For example, TA1 antibody specifically binds the prothrombin C9 peptide as determined by Western blotting (See e.g., FIGS. 4B, 9B and 10B).

In the above-described methods, amino acids used to mutagenize the TA1 binding site and one or more of the C9 amino acid residues were typically conservative or non-conservative amino acid replacements. Referring now to FIGS. 15A and 15B, an amino acid (D or L form) not under the "replace with" column, was a non-conservative amino acid replacement with respect to the amino acid in the "for amino acid" column. Accordingly, a tyrosine contact residue replaced with phenylalanine would represent a conservative amino acid replacement, whereas an arginine contact residue replaced with alanine would represent a non-conservative amino acid replacement.

In general, mutated TA1 antibodies were made by independently mutagenizing the TA1 $V_H$ or $V_L$ DNA sequence (see FIGS. 1 and 2) at a site which encoded a contact residue. The mutated $V_H$ or $V_L$ DNA sequence was then recombinantly joined to a DNA vector encoding an operatively linked antibody heavy chain (HC) or light chain (LC) gene, respectively. More specifically, if the $V_H$ DNA sequence was mutated at the site encoding the contact residue, it was operatively joined to a DNA vector encoding the HC gene of the vector. Similarly, if the $V_L$ gene was mutated, it was operatively joined to a vector encoding the LC gene. By appropriately co-expressing each of the DNA vectors in a suitable cell, a mutated TA1 antibody was formed which included a mutated contact residue. It will be appreciated that the mutated TA1 antibody was a chimeric molecule encoded by a mutated TA1 $V_H$ or $V_L$ DNA sequence, an unmutated TA1 $V_H$ or $V_L$ DNA sequence, and an appropriate operatively joined HC and LC gene. Accordingly, the parental (unmutated) TA1 antibody was also a chimeric molecule.

By the term "appropriate co-expression" or similar term is meant that the DNA vectors were introduced into a suitable cell (by, e.g., transfection, electroporation or biolistic transfer) such that the vectors independently expressed i) a suitable isolated DNA of the invention operatively linked to an immunoglobin heavy chain constant domain; or ii) a suitable, isolated DNA of the invention operatively linked to a light chain constant domain. When introduced into the same suitable cell, polypeptides expressed from the vectors combine and form an antibody capable of specifically binding the C9 antigen.

Complex formation between antigens and antibodies is generally assisted by the formation of hydrogen bonds between contact residues. However, in some cases, contact residues may form ionic bonds. For example, ionic bonds can form between suitably positioned R groups of amino acids such as the $—COO^{31}$ group of aspartate and the $—NH_3^+$ group of lysine. Ionic bond distances are generally described by Coulomb's Law and are typically within about 1 Å to 4 Å, preferably about 2 Å–3 Å, most preferably about 2.8 Å. In accordance with the present methods, if a suitably positioned three-dimensional model of a first binding molecule specifically bound to a second binding molecule shows two oppositely charged amino acid side groups less than about 5 Å from each other, the model can be positioned and refined to bring the charged side groups within an acceptable Coulomb bond distance. Accordingly, unacceptable electrostatic hindrance may occur if the two oppositely charged amino acid side groups are not within an acceptable Coulomb bond distance.

As outlined above, the methods of the present invention are suitable for identifying contact residues in antibodies and antigens. However, the present methods can also be suitably used to identify contact residues in other binding molecules such as SH2 binding domains, MHC molecules, e.g., an MHC II-peptide complex (Stern, L. J. and D. C. Wiley, supra); and the single-chain (sc-)MHC class I or class II complexes disclosed in said published PCT Application No. WO 96/04314 and said pending U.S. application Ser. No. 08/596,387. The sc-MHC complexes include empty single-chain MHC complexes (no presenting peptide), and sc-MHC complexes with recombinantly fused or loaded presenting peptide. Accordingly, the specific binding affinity of the SH2 and MHC molecules can be improved in accordance with the present methods.

The improved SH2 and MHC molecules provide a number of significant advantages. For example, improved empty sc-MHC molecules (class I or II), can be used to screen for a large number of presenting peptides, e.g., presenting peptides which exhibit low binding affinity for the parental sc-MHC molecule. Presenting peptides identified in the screen can then be used to make a loaded sc-MHC molecule with improved capacity to bind the presenting peptide after loading the presenting peptide. Additionally, the presenting peptide can be sequenced in accordance with well-known methods, and then recombinantly fused to the MHC complex in accordance with methods disclosed in said published PCT Application and said pending U.S. Application. Exemplary peptides include those associated with or suspected of being associated with an allergy and/or autoimmune disorder such as Der p I, Fel d I, Amb a I, Amb aV; or immunologically-reactive epitopes thereof no larger than about 15 amino acids. MHC molecules with increased affinity for a presenting peptide can be tested in T cell assays disclosed in said published PCT Application or said pending U.S. Application, to see if the presenting peptide is capable of modulating T cell activity.

The present methods can be readily adapted to identify contact residues in binding molecules such as receptors and ligands for which apparent X-ray crystallographic structure is available. By the term "apparent" is meant that the X-ray structure of at least a fragment of the binding molecule is known, which fragment is responsible for specific binding as judged by binding assays such as gel mobility shift assay. For example, with respect to a receptor, the fragment would include amino acid contact residues which specifically bind the ligand. Alternatively, if the X-ray structure of the fragment is not known, it is at least 90% homologous, preferably at least 95% homologous, and more preferably at least 99% homologous to another fragment of known X-ray structure. In either case, the above-described method is adapted by substituting the interactive graphic display software packages with conventional straight homology modeling programs and verifying the three-dimensional models of the binding molecules with those in the PDB database.

The term "homology" as used herein in reference to an amino acid sequence, refers to the extent of amino acid sequence identity between polypeptides. When a first amino acid sequence is identical to a second amino acid sequence, then the first and second amino acid sequences exhibit 100% homology. The homology between any two polypeptides is a direct function of the total number of matching amino acids at a given position in either sequence, e.g., if half of the total number of amino acids in either of the two sequences are the same then the two sequences are said to exhibit 50% homology.

The TA1 antibody, improved TA1 antibodies, C9 antigen, and improved C9 antigens were prepared in accordance with the present methods and conventional procedures. Plasmids carrying the TA1 $V_L$ DNA Sequence of FIG. 1 (SEQ ID NO. 40) or the TA1 $V_H$ DNA Sequence of FIG. 2 (SEQ ID NO. 42) have been deposited with the American Type Culture Collection (ATCC), Rockville, Md. 20852 USA. The ATCC designation numbers are 97720 (TA1 $V_L$) and 97721 (TA1 $V_H$).

Conventional procedures were also used to make vector DNA, cleave DNA with restriction enzymes, ligate and purify DNA, transform or transfect host cells, culture the host cells, and isolate and purify proteins and polypeptides. See generally Sambrook et al., *Molecular Cloning* (2d ed. 1989), and Ausubel et al. supra. Examples of cells which can express isolated DNAs encoding the antibodies disclosed herein include bacterial cells (e.g., *E. coli* and *B. subtilis*) such as, e.g., MM294, DM52, XL1-blue (Stratagene), animal cells (e.g., NSO, CV-1, CHO cells), yeast cells (e.g., *S. cerevisiae*), amphibian cells (e.g., *Xenopus oocyte*), and insect cells (e.g., *Spodoptera frugiperda* or *Trichoplusia ni*). Methods of expressing recombinant DNA in these cells are known, e.g., see Sambrook et al., *Molecular Cloning* (2d ed. 1989), Ausubel et al. supra, and Summer and Smith, A Manual of Methods for Baculovirus Vectors and Insect Cell Culture Procedures: *Texas Agricultural Experimental Station Bulletin* No. 1555, College Station Tex. (1988).

The term "vector" as used herein means any nucleic acid sequence of interest capable of being incorporated into a host cell and resulting in the expression of a nucleic acid sequence of interest. Vectors can include, e.g., linear nucleic acid sequences, plasmids, cosmids, phagemids, and extra-chromosomal DNA. Specifically, the vector can be a recombinant DNA. Also used herein, the term "expression" or "gene expression", is meant to refer to the production of the protein product of the nucleic acid sequence of interest, including transcription of the DNA and translation of the RNA transcript.

In many cases, it will be desirable to carry an isolated DNA of the invention in a suitable vector for expression in cells capable of expressing the isolated DNA. Typically, the vector will further include DNA sequences necessary for expression in the cell, as well as DNA sequences encoding an operatively linked heavy chain or light chain constant domain. Examples and uses of such vectors can be found in, e.g., Near, R. I. et al. *Mol. Immunol.* 27: 901 (1990); Near et al. *Mol. Immunol.* 30:369 (1993) and references cited therein.

Additionally, it may be desirable to replicate an isolated DNA of the invention in a suitable vector without necessarily expressing the DNA. For replication in prokaryotes, such vectors may include (i) an origin of replication functional in *E. coli* and derived from, e.g., pBR322; (ii) a selectable antibiotic resistance gene also derived from pBR322 (e.g., tetracycline); (iii) a transcription termination region, e.g., the termination region of the *E. coli* trp operon (placed at the end of the tetracycline resistance gene to prevent transcriptional read-through into the trp promotor region; (iv) a transcription promotor, e.g., the trp operon promotor or the lac promoter; (v) an isolated DNA of the invention; and (vi) a transcription terminator, e.g., the T1T2 sequence from the ribosomal RNA (rrnB) locus of *E. coli*. Other suitable vectors, e.g., for replication in eukaryotic cells are known in the art (see e.g., Sambrook et al. supra; Ausubel et al. supra).

The present invention features isolated DNAs which independently encode a TA1 $V_H$ or $V_L$ region polypeptide, or a polypeptide homologous to the TA1 $V_H$ or $V_L$ polypeptide. The term "isolated," as used herein, refers to a nucleic acid segment or fragment which is not immediately contiguous with (i.e., covalently linked to) both of the nucleic acids with which it is immediately contiguous in the naturally occurring genome of the organism from which the DNA is derived. The term, therefore, includes, for example, a DNA which is incorporated into bacteriophage, virus (i.e., mammalian or insect virus) or plasmid vectors capable or autonomous replication in an eukaryotic, prokaryotic, or insect cell host. The term also includes a nucleic acid which exists as a separate molecule independent of other nucleic acids such as a nucleic acid fragment produced by chemical means, PCR, or restriction endonuclease treatment.

The invention also features substantially pure antibodies and improved antibodies (or antigen-binding fragments thereof). As used herein, the term "substantially pure" in reference to an antibody, other protein (or polypeptide) describes a protein or polypeptide which has been separated from components which naturally accompany it. For example, with standard immunoaffinity chromatography, the TA1 antibody can be purified by using the C9 antigen. Typically, a protein or polypeptide is substantially pure when at least 50% of the total material (by volume, by wet or dry weight, or by mole per cent or mole fraction) is a protein or polypeptide of the invention. Preferably the protein or polypeptide is at least 50%, more preferably at least 75%, even more preferably at least 90%, and most preferably at least 99% of the total material. Purity can be conveniently assayed by well known methods such as SDS-PAGE gel electrophoresis, column chromatography such as, e.g., affinity chromatography, or HPLC analysis.

It is possible to isolate a DNA sequence from a library (e.g., a cDNA, genomic or phage display library), which is capable of hybridizing to the DNA sequence shown in FIG. 1 or 2 under high stringency conditions. Generally, to obtain the DNA sequence, the isolated DNA is detestably labelled with, e.g., $^{32}P$, $^{35}S$, biotin, or other suitable label in accordance with standard methods. The labelled DNA is then used to probe the library under high stringency conditions, and the DNA sequence thus identified is purified by routine screening methods (see e.g., Ausubel et al. supra, and Sambrook et al. supra). Once purified and sequenced, the DNA sequence will preferably be between about 90 to 500 nucleotides in length, more preferably between about 100 to 350 nucleotides in length. In most cases, the DNA sequence can be recombinantly inserted into a suitable vector which includes an operatively joined heavy or light chain constant domain (see FIG. 3). Suitably, the DNA sequence will be capable of forming an F1.2 binding domain with the TA1 $V_H$ or $V_L$ domains.

By the term "high stringency conditions" is meant the solution hybridization of one nucleic acid to another nucleic acid under well-known conditions (see e.g., Sambrook et al., infra., Ausubel et al. supra). For example, a high stringency hybridization can be performed at about 42° C. and 50% formamide, followed by a first wash at about 65° C. in about 2× SSC, and about 1% SDS; followed by a second wash at about 65° C. and about 0.1% SDS. Stringency conditions for hybridizing the nucleic acids can be conveniently established by first performing a conventional Southern blot hybridization.

The antigens, presenting peptides and other polypeptides disclosed herein can be made, e.g., by routine organic chemical synthesis, or cleaved from a larger protein containing the polypeptide. For example, organic chemical synthesis can be performed by conventional methods of automated peptide synthesis, or by classical organic chemical techniques.

In some cases, a binding molecule will have the same function in different organisms. For such a binding molecule, candidate contact residues can be identified by analyzing how the amino acid sequence of the binding molecule changes between the organisms. For example, if the binding molecule is present in humans, rats, and mice, it is likely that at least some of the contact residues will be the same in each organism. Non-contact residues will generally be different between the organisms. By comparing the amino acid sequence of the human binding molecule (or a suitable portion thereof) to the corresponding amino acid sequence in the rats and mice, it is possible to identify candidate contact residues as those amino acids which remain the same in each organism. Candidate contact residues identified in this way can be tested by the methods described herein to identify contact residues.

The following non-limiting examples are illustrative of the invention:

EXAMPLE 1

Construction of the PenI fusion Vector pCC50

The PenI protein was used to carry various mutated C9 antigens in the form of PenI-C9 fusion proteins. To construct the pCC50 vector containing the penI gene, the penI gene (T. Himeno et al., *J. Bacteriol,* 68: 1128–1132 (1986); Wittman, et al., *J. Bacteriol,* 170: 32006 (1988) was amplified by PCR using standard techniques and the plasmid pCC34 as template. The plasmid pCC34 was derived from a PUC19 vector containing the penI gene. Conditions of the PCR were as follows: 100 ng of the plasmid pCC34 was used as template, 10 pmoles of the primers FX-1 and FX-2 (identified immediately below), 50 mM KCl, 20 mM Tris-HCl pH 8.4, 2 mM $MgCl_2$, 100 μg/ml Bovine Serum Albumin, 50 μM dNTP, 2.5 units of Taq DNA polymerase (Cetus Perkin-Elmer) in a 100 μl final volume. The reaction was run for 25 cycles at 95° C., 55° C. and 72° C. The penI gene also could be amplified by standard PCR techniques directly from *Bacillus liceniformis* chromosomal DNA using these same primers. The above-mentioned PCR primers used to amplify the penI gene were:

Upstream primer (FX-1)

5'-GGAAGCTTATGAAAAAAATACCTC-3' (SEQ ID NO:44:)

Downstream primer (FX-2)

5'-GGGGATCCCTCACCATGGTTCCTTCTTT-CTGTTC-3' (SEQ ID NO:45:)

The upstream PCR primer was designed to add a HindIII restriction site at the 5' end of the PCR product and the downstream PCR primer was designed to add NcoI and BamHI restriction sites at the 3' end of the PCR product. The PCR product was digested with HindIII and BamHI and cloned into the HindIII-BamHI sites of the *E. coli* vector pUC19. As a result, this vector (tET002-3) contains the penI gene construct flanked by HindIII at the 5' end and NcoI and KpnI at the 3' end. The sequence of the cloned penI gene was confirmed using the ABI DNA sequencing apparatus and the M13 (+/−) universal sequencing primers.

To demonstrate that a fusion peptide could be expressed at high levels in *E. coli* the following oligonucleotides were designed and synthesized by the ABI oligonucleotide synthesizer:

Upstream primer (ET003)

5'-CATGGGACTCTGACCGTGCAATCGAAG-GTCGTTGAGGGATCCGGTAC-3' (SEQ ID NO:46)

Downstream

5'-CGGATCCCTCAACGACCTTCGATTG-CACGGTCAGAGTCC-3' (SEQ ID NO:47)

These oligonucleotides were annealed to each other as described below and cloned into the NcoI-KpnI site of the plasmid tET002-3. 100 pmoles of each oligonucleotide were boiled for 10 minutes in the presence of 44 mM EDTA and 66 mM NaCl and cooled slowly to room temperature. These annealed oligos where cloned into the NcoI-KpnI sites at the 3' end of the penI gene. This plasmid was designated pCC50.

EXAMPLE 2

Computer modeling of the TA1 antibody binding site.

A three-dimensional model of the TA1 antibody binding site was constructed using the Oxford Molecular ABM™ software (Rees et al., supra) on the Silicon Graphics Indigo 2 Extreme system (Silicon Graphics). The model was energy minimized using Insight II software (Biosym). A photograph of the three-dimensional model of the TA1 binding site is shown in FIG. 5.

Based on the lengths of the TA1 light chain CDRs, the TA1 binding surface was similar in many respects to other antibody binding surfaces. These have been described as a cavities or grooves which are characteristic of hapten or peptide binding antibodies (see e.g., Wang et. al., *Mol. Immunol.* 28:1387–1397 1991).

To verify the antibody structure, Procheck (Laskowski et. al., *J. Appl. Crystallogr.* 26:283–291, 1993) analysis was performed on the three-dimensional model of the TA1 antibody binding site. The program presented results as a Ramachandran plot (see FIG. 8A), which in this case showed 81.3% of the TA 1 residues in the most energetically favored regions with 3% (6 total residues) being in generously allowed or disallowed regions. Three of these aberrant residues were within the TA1 heavy chain and three are within the TA1 light chain.

In general, CDRs can be grouped into canonical classes based on amino acids within the CDR loops which help define secondary structure (see e.g., Searle, S. J. et al. supra; Chothia et al. supra ). To determine if any of the six residues defined a canonical class and thus played a role in determining the topography of the binding surface, the TA1 amino acid sequence was aligned to those of the canonically grouped antibodies. The TA1 model was also analyzed to determine if the six residues were positioned in or near the TA1 binding surface. Using this approach, one of the aberrant residues, Met 56 in L2, was directly adjacent to Arg 55, a residue which formed a hydrogen bond with C9 in the initial TA1-C9 complex model (see below and FIG. 1). The remaining residues were either in regions distant from the binding surface or in a region where the amino acid sequence was nearly homologous to an X-ray resolved canonical loop; therefore having no substantial effect on model accuracy. Accordingly, the three-dimensional model of the TA1 binding surface was an accurate depiction of the antibody binding site and reasonably accurate for use as a docking constraint.

EXAMPLE 3

Construction, purification and testing of C9 peptide mutants

The nine amino acid peptide C9 (DSDRAIEGR SEQ ID NO:48), corresponds to the carboxyl terminus of the F1.2 polypeptide of prothrombin. To make mutated C9 antigens, each of the nine amino acids of the peptide were independently and consecutively mutagenized by annealing complementary oligonucleotides containing the C9 coding region, individual mutations and the umber stop codon. The oligonucleotides are disclosed in FIG. 12 and SEQ ID NOs: 1–25.

The annealed oligonucleotides were cloned as NcoI-BamHI cassettes into the vector pCC50. The resulting plasmids were used to transform strain DG101 (endA thil hsdR supE44 lacI$^q$ lacZ$\Delta$m15 F$^-$) obtained from David Gelfand. The PENI-C9 fusion genes were then subcloned as HindIII-BamHI cassettes into pDG160, a derivative of pFC54.t (Wang et. al, Science 228:149–154, 1985). The resulting plasmids were used to transform strain DG116 (thi-1 hsdR17 endA1 supE44 [$\mu$ cI857 $\Delta$H1 bioT76]) obtained from D. Gelfand.

The DG116 cells include a pDG160 backbone vector (parent expression vector of the PenI-C9 fusion constructs) which includes a PL promoter controlled by a constitutively expressed repressor produced by the DG116 cells. When the cells are grown at 37° C., the repressor is non-functional, thereby activating the PL promoter. Other E. coli strains carrying compatible heat induction vector systems can also be used (see e.g., Ausubel et al. supra).

Heat induction was performed in accordance with known procedures (see e.g, Greenfield et. al., Bio/Technology 4:1006–1011, 1986). The resulting PENI-C9 protein fusions were independently purified by known methods (see e.g., Wittman and Wong, J. Bacter. 170, 7:3206–3212, 1988), except that a 35% ammonium sulfate cut was performed rather than a 50% ammonium sulfate cut, followed by monodisperse cation exchange (Mono-S) chromatography essentially in accordance with the instructions of the manufacturer (Pharmacia, Uppsala, Sweden). Protein concentrations were determined using the BCA protein assay (Pierce).

Western blot analysis of the penI-C9 fusion proteins was performed essentially in accordance with standard methods (see, e.g., Ausubel et al. supra, Harlow and Lane, Antibodies: A Laboratory Approach CSHSQB (1988). For example, purified PENI-C9 fusion proteins were loaded at 1ug/well and electrophoresed on a 15% SDS-PAGE gel. The gel was transferred onto a membrane (Immobilon membrane from Millipore) using the Semi-dry blotting method (see, e.g., Kyhse-Andersen, J., J. of Biochem. and Biophys. Methods 10:203–209, 1984). The blot was then blocked for 15 min at room temperature in 1× blotto (9.8mM NaPO$_4$ pH 7.4, 1% skim milk, 1% NP-40) and then incubated with TA1 monoclonal antibody. Typically, the TA1 antibody was first diluted in 1× blotto to a final concentration of about 2.71 $\mu$g/mL for at least 1 hour at room temperature. The blot was subsequently washed and incubated with 1:10,000 goat antimouse IgG HRP (Jackson Lab) diluted in 1× blotto for 30 min at room temperature and then washed and developed with ECL chemiluminescent reagent (Amersham) and exposed to X-ray film for about 30 seconds and developed. Signal intensity can be estimated by conventional densitometry.

Purified PENI-C9 fusion proteins were also tested for binding to the TA1 antibody by using a competition EIA (Enzyme Immuno Assay). Briefly, microtiter plates (96 well variety from Nunc) were passively coated overnight at 4° C. with 100 ng/well of wild-type PENI-C9 (i.e., parental and non-mutated C9 peptide). Serial dilutions of each individual PENI-C9 fusion protein was made in conjugate diluent (19.6mM Tris-HCl, 244.8mM NaCl, 0.1% Tween-20, 2% Gelatin) and preincubated for 1 hour at room temperature with TA1 (final concentration 271 ng/mL). The coated microtiter plates were washed and 100 $\mu$L of each preincubated sample was added to each well. Each plate was then incubated for 30 minutes at room temperature. The plates were washed and 100 $\mu$L of diluted (1:2000) goat anti-mouse IgG HRP diluted in conjugate diluent was added to each well and the plates were incubated for 30 minutes at room temperature. The plates were washed for a final time and 100 $\mu$L of ABTS substrate (Kirkegaard & Perry Laboratories) was added to each well and allowed to incubate at room temperature for 8 minutes. The reaction in each well was quenched with 100 $\mu$L of 1% SDS stop solution. The signal was then read at 405 nm. Each dilution was performed in triplicate and the results were averaged. The maximum signal (100%) was defined as the signal for PENI preincubated with TA1 (control experiment). The concentration of Pen I-C9(wt) preincubated with TA1 that resulted in a signal that was half the maximum signal was defined as 50% inhibition and all Pen I-C9 mutated fusion proteins were compared at this concentration. More specifically, the Pen I maximum signal was the signal resulting from Pen I by itself (no fused C9) preincubated with the TA1 antibody. Pen I should not be specifically bound by TA1. Accordingly, when the pre-incubated material was applied to the Pen I-C9 WT coated wells, there should be no competition for the TA1 binding sites and signal saturation of all the TA1 binding sites to the immobilized, excess Pen I-C9 WT should be achieved.

As discussed above, each consecutive amino acid of C9 was substituted with alanine, with the exception of Ala #5 (i.e. the alanine at position 5 of the C9 peptide) which was replaced with Ser. Western blots of each mutant PENI-C9 fusion protein are shown in FIGS. 4B, 9B, and 10B. The corresponding Coomassie stained gels in FIGS. 4A, 9A, and 10A show that about the same amount of PENI-C9 fusion was produced in each lane.

The results of the EIA analysis of various PENI-C9 fusion proteins is presented in FIG. 13.

The specific binding affinity of TA1 for each individual PENI-C9 fusion protein was also determined by biospecific interaction analysis (BlAcore) in accordance with the manufacturer's instructions (Phamacia-Biosensor). In general, BlAcore is a biosensor system which uses surface plasmon resonance as a detection means (see e.g., Altschuh et. al., Biochem. 31:6298–6304, 1992).

To perform BIAcore analysis, TA1 was immobilized onto the surface of a CM5 sensor chip using the amine coupling kit and procedures provided by the manufacturer. The procedures include activation of the sensor chip with 30 1L of a 1:1 mixture of 11.5 mg/mL N-hydroxysuccinimide and 75 mg/mL N-ethyl-N'-(dimethylaminopropyl) carbodimide then injecting 5 µL of TA1 (diluted to 57 ug/mL in 10 mM sodium acetate buffer pH4) at a flow rate of 3 µL/min. Residual dextran binding sites were inactivated by treating the chip surface with 35 µL of 1M ethanolamine pH 8.5. The resulting TA1 immobilized onto the chip was approximately 4500 resonance units (RU). The purified PENI-C9 fusion proteins were diluted to 30 ug/mL in BIAcore eluent buffer (10 mM HEPES, 150 mM NaCl, 3.4 mM EDTA, 0.005% P20 surfactant, pH7.4). For each PENI-C9 fusion protein injected, a relative response in RU, representing the amount of PENI-C9 bound, was calculated. Percent of binding was calculated by setting the relative response of PENI-C9 (wt) to 100%.

The results of the BIAcore analysis are presented in FIGS. 11 and 13 which follow.

The SDS electrophoresis, Western blot, competition EIA, and Biocore results indicated the approximate location of contact residues in the antigen. For example, the results demonstrated that when either Ile #6, Gly #8 or Arg #9 (C9 antigen) was replaced with Ala, specific TA1 binding was decreased or eliminated compared to the specific binding of the parental C9 antigen. Further, when Glu #7 was substituted with Ala, specific binding increased compared to parental C9 (it also increased with respect to any other mutated C9 peptide).

To determine if the carboxy terminus of C9 also interacted with the TA1 binding surface, competition EIA was performed on a C9 peptide chemically modified to include a terminal carboxy amide group instead of a hydroxyl. The chemically modified C9 peptide did not bind TA1.

The results indicated that residues in the carboxy terminal half of C9, depicted here as "XXXXAIXGR (SEQ ID NO:49)", had the greatest influence on the specific binding affinity of TA1. Further, the Glu #7 mutation increased specific binding affinity for the TA1 antibody. It appears that by replacing the bulkier Glu sidechain with the smaller Ala sidechain, the TA1-C9 binding surface was optimized, thereby increasing the specific binding affinity for the mutated C9 antigen. This binding data was used in combination with interactive graphic display to position the C9 epitope into the TA1 binding clefts, to produce a three-dimensional model of the TA1-C9 complex.

By the term "increased specific binding affinity" or similar term is meant the greater specific binding strength of an improved binding molecule, as opposed to the specific binding strength of the corresponding parental molecule as judged by western blot binding assays.

EXAMPLE 4
Computer Modeling of the initial TA1-C9 complex

An alignment search for the C9 sequence was performed without finding any suitable alignments in the PDB database. A suitable alignment has a string with at least 4 adjacent amino acids in the primary sequence of C9, homologous to the primary sequence of structures in the PDP database. Consequently, when a suitable alignment was found, it was generally reasonable to assign the same three-dimensional coordinates to (or model) homologous amino acids. Therefore, the C9 epitope was conceptually constructed by using the Insight II Builder Module program to assemble the amino acid sequence in a linear-planar conformation and, based on the binding data from alanine-scan mutagenesis (see Example 3) and the binding site constraints of the three-dimensional representation of the TA1 binding surface (see Example 2), a three-dimensional model was produced which showed the C9 epitope docked into the TA1 binding cleft. See FIG. 6.

Figure 6:
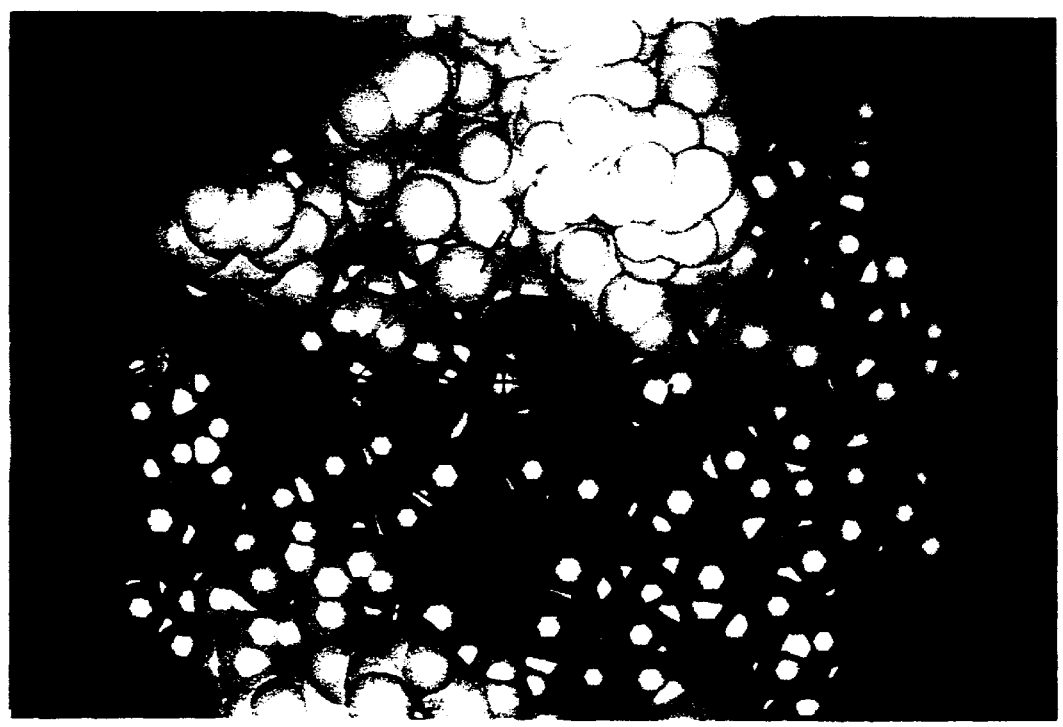

The TA1-C9 complex model shown in FIG. 6 was further manipulated by the following methods:

1) Modification of dihedral angles: Dihedral bond angles along the C9 polypeptide backbone were modified to allow the peptide to fit within the spatial constraints of the TA1 binding cleft (rendered in VDW surfaces), and to form suitable binding interactions consistent with the observed C9 and TA1 binding data. Favorable VDW interactions were also maintained by keeping the distance between the represented atoms within an acceptable VDW radius. Preferred dehedral bond angles were those which prevented the C9 backbone and sidechains from folding onto itself and penetrating C9 VDW surfaces.

Typically, VDW radii are the sum of the contact radii of the atoms involved in a VDW interaction. For the atoms H, C, N, O, S, and P, the radii are approximately 1.2 Å, 2.0 Å, 1.5 Å, 1.4 Å, 1.85 Å, and 1.9 Å, respectively. For example, the VDW radii between carbon and nitrogen would be about 2.0 Å+1.5 Å=3.5 Å. Accordingly, an unacceptable VDW distance between carbon and nitrogen would be any distance substantially below about 3.5 Å.

2) Monitor hydrogen bonding between the C9 peptide and the TA1 antibody binding site: Translational and rotational movements were used to position the C9 peptide so that hydrogen bonds would be consistently formed between Arg 9 in C9 and the TA1 binding site while the C9 peptide remained within the TA1 binding cleft. Arg 9 was a candidate contact residue as judged by Western blot (FIGS. 4B, 9B, competitive EIA and Biocore analysis (FIGS. 11, 13)). Additionally, the sidechain of this Arg is a prospective H bonding partner and the residue is at the carboxy end of the molecule.

3) Optimize (steep sloped energy minimization) the C9 epitope: This procedure involved repositioning C9 to form the most hydrogen bonds, less than or equal to about 2 Å, with TA1 while minimizing bumping to ensure that C9 was not penetrating any VDW surfaces on the TA1 cleft. Bumping parameters were generally pre-set by the general modeling software. For example, the Insight II software has a bump function default of about 2.5 Å from atom center to atom center.

4) Energy minimize the C9 epitope: This procedure did not cause a substantial change in the overall antibody-antigen conformation. Energy minimization programs are typically provided as part of a general modeling software program. In general, the energy minimization program modeled the three-dimensional representation of C9 into the closest low energy state from the present coordinate placement of the three-dimensional model. One acceptable energy minimization program is CHARMM, available as part of the Insight II software.

The three-dimensional model of the TA1 antibody and C9 antigen complex resulting from manipulations 1–4 above, is sometimes referred to herein as "initial TA1-C9 complex".

The initial TA1-C9 complex model was consistent with the TA1 binding results observed in previous examples. In addition, the initial TA1-C9 complex model was identical to a more refined version (see below and FIGS. 7A–7F which follow) of the model with two exceptions: 1) The Arg 9 sidechain was more linear and formed only one hydrogen bond with Arg55 in L2 and, 2) the carboxyl group at the carboxy terminus of C9 formed a hydrogen bond with Tyr213 in H3. Both of these characteristics were consistent with the binding knockout observed when Arg 9 was substituted with Ala and when the carboxy terminus hydroxyl was replaced with an amide group.

The initial TA1-C9 complex model was examined for conformity with structural characteristics observed in other antigenic peptides of known structure. As can be seen in FIGS. 7A–7F of the refined TA1-C9 complex model (see below) the C9 peptide does not conform to the binding surface of TA1 as an extended linear structure. Instead, it appears to take on a structured β-turn form to fit into the binding cleft, suggesting that the peptide has a conformational preference for structured form. This observation is consistent with many short antigenic peptide epitopes (for review see Dyson and Wright, *FASEB J.* 9:37–42, 1995).

Figure 8A:
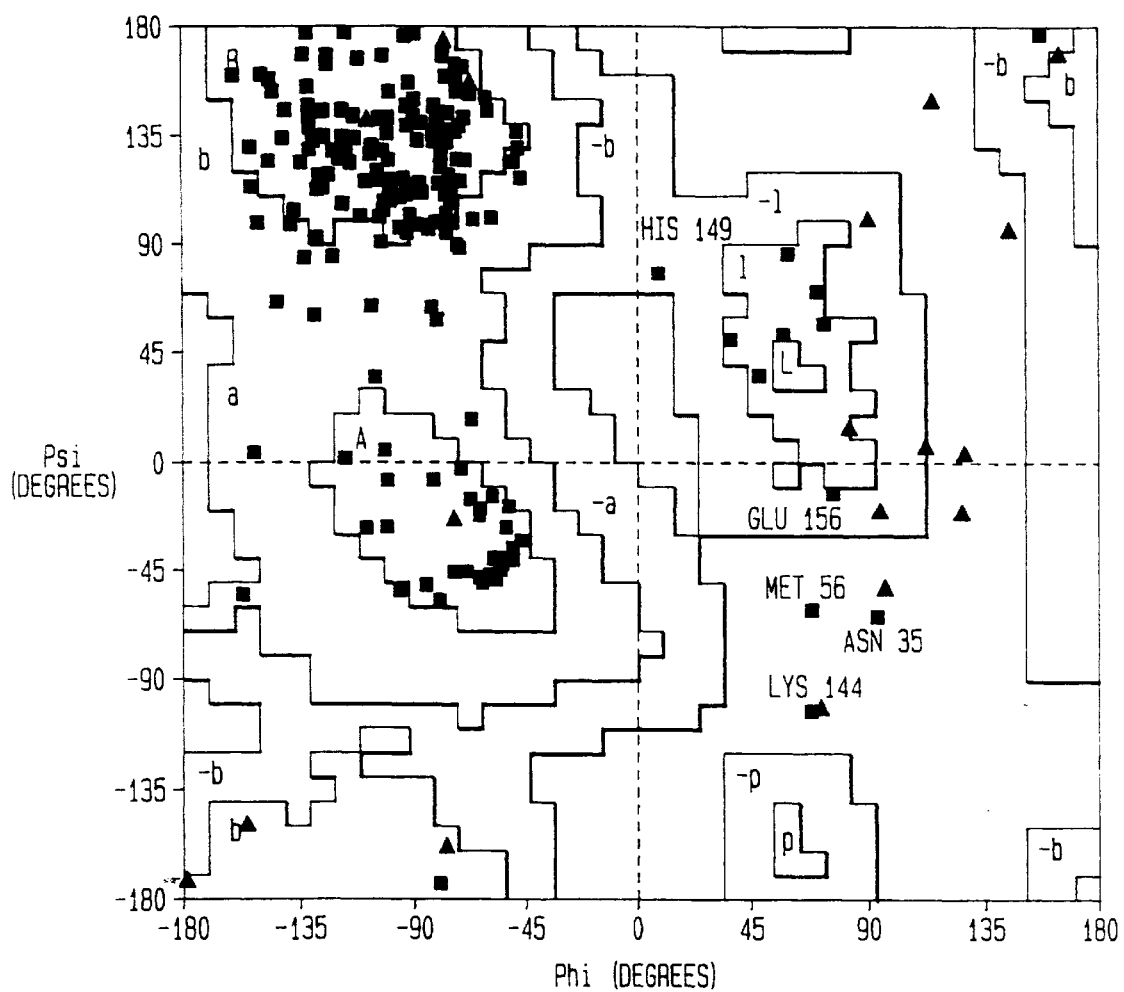
Figure 8B:
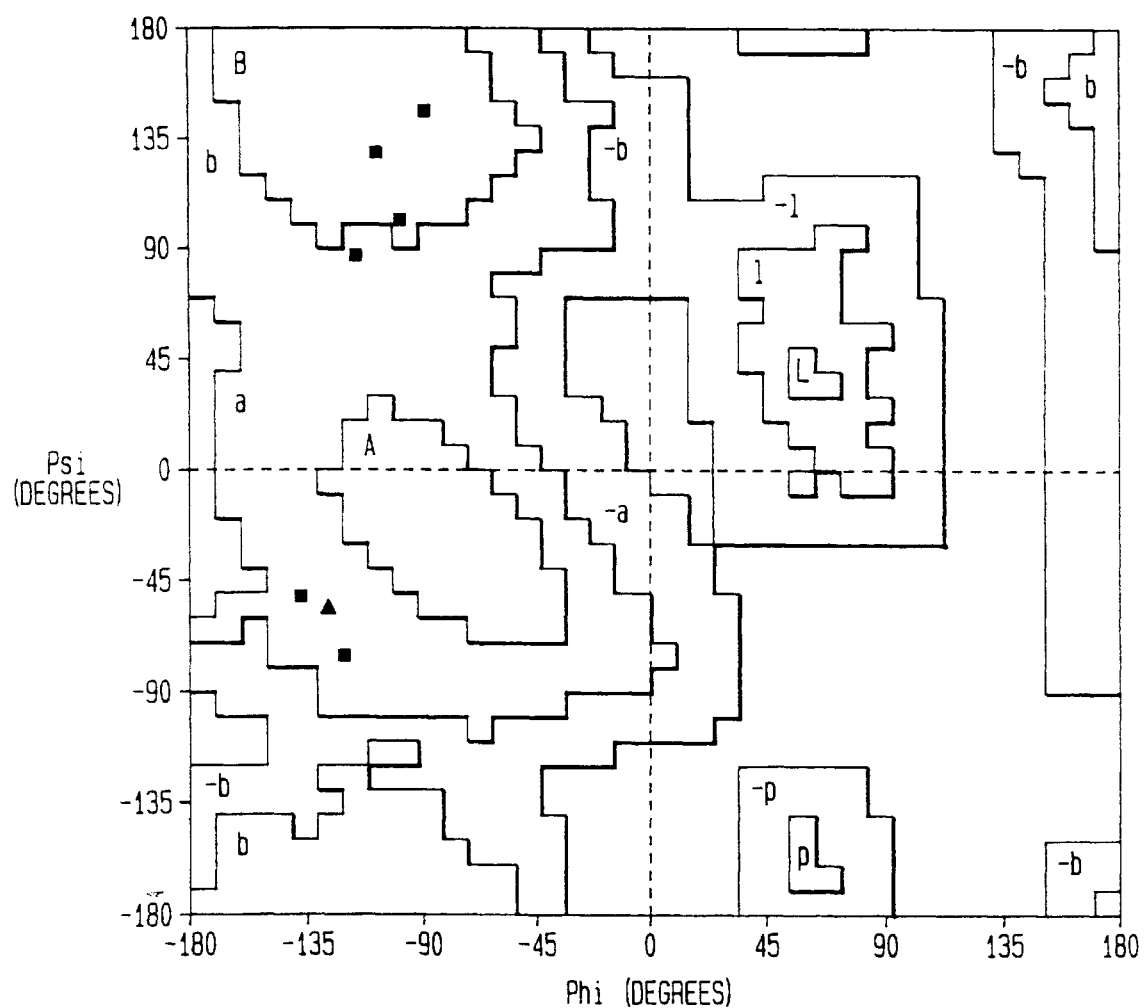

The initial TA1-C9 complex model was also examined for conformity by conventional Ramachandran plot analysis (see FIG. 8B). The Ramachandran plot shows that the amino acid residues fall within energetically allowed regions. By this criterion the polypeptide backbone geometry detected by the methods described herein is of suitable quality. Furthermore, there is no significant penetration of VDW surfaces within C9 or at the binding interface with TA1. However there is a hole at the interface, between the H3–H2 loops of TA1 and the middle of C9. It seems that this area is closed off by H3 during complex formation.

EXAMPLE 5

Identification and Testing of Additional Candidate Contact Residues.

The initial TA1-C9 complex model (see Example 4 and FIG. 6) provided a blueprint for identifying contact sites in the TA1 antibody and C9 antigen. By inspection of the initial TA1-C9 complex model, additional candidate contact residues in the C9 peptide were seen near suitably positioned amino acids in the TA1 binding site: Arg 9 (sidechain hydrogen bond), Glu 7 (sidechain is positioned between L3 and L1), Ile 6 (sidechain may exclude water), Ala 5 (cl carbon backbone amine hydrogen bond), Arg 4 (sidechain hydrogen bond), Asp 3, Ser 2, and Asp 1 (sidechains are free of any interaction with TA1).

To confirm that these C9 amino acids were candidate contact residues, SDS-electrophoresis, Western blot analysis competition EIA and Biocore conducted using mutated C9 peptides (as PEN1-C9 fusions) (see FIGS. 4B, 9B, 10B, 11 and 13 which follow). The binding results of the mutations relative to each other compare well except in the case of the Ala5Cys mutation (see FIGS. 4B). Taken together with the binding data presented in Example 3, the present results identified the following candidate C9 contact residues Ile6, Gly8, Arg9, Glu7, Ala5, Arg4.

EXAMPLE 6

Identification and Testing of TA1 Contact Residues.

TA1 antibody contact sites were identified as those amino acid residues about 2A from the candidate contact residues identified in the preceding Example. The TA1 contact residues were as follows: Arg55 in L2 (hydrogen bonded with Arg 9), Tyr213 in H3 (hydrogen bonded with the carboxy terminus), Tyr37 in L1 (in proximity to C9), Trp164 in H2 (hydrogen bonded with Ala 5), and His96 in L3 (hydrogen bonded with Arg 4). TA1 antibodies were mutated at these sites (see below) and then analyzed for specific C9 binding by using BIAcore (see e.g., FIG. 11). As controls, TA1 antibodies were also mutated at the following non-contact residues (Leu30 in L1, Phe99 in H3, or Tyr218 in H3 (see FIG. 11).

The results depicted in FIG. 11 show that the Tyr 37 Phe and Arg 55 Lys mutations strongly decreased binding to the C9 peptide in agreement with the refined TA1-C9 complex model presented in FIGS. 7A–7F. FIG. 11 also shows that TA1 contact residues, Tyr213, Tyr37, Trp164, and His96 contributed to the TA1 binding cleft. However, surprisingly, substitution with phenylalanine at Tyr37 lowered overall TA1 binding affinity, whereas substitution with phenylalanine at Tyr213 substantially increased TA1 binding affinity for C9. The result was surprising in part because phenylalanine substitution should not substantially alter sidechain volume and a potential hydrogen bonding group (tyrosine) is removed by the substitution. The lowered binding affinity of the Tyr37Phe mutation is also surprising because no hydrogen bond was believed to exist at position 37. Accordingly, the initial TA1-C9 complex model was refined in the following example.

EXAMPLE 7

Refinement of the Initial TA1-(9 Complex Model.

The initial TA1-C9 complex model was refined with respect to the specific binding affinity of the above-mentioned contact residues.

The C9 peptide was positioned to form a hydrogen bond with Tyr37 and to remove the hydrogen bond between Tyr213 and the C9 carboxy terminus. During the positioning of C9, overall C9 α-carbon backbone conformation and other hydrogen bonds were maintained. To achieve this manipulation, the C9 epitope was translated approximately 0.1 Å along the y-axis towards the light chain, thus breaking the Tyr213-carboxy terminal hydrogen bond. The dihedral angles of the atom bonds along the Arg 9 sidechain and α-carbon were modified and when the sidechain was adjusted to lie closer to the C9 α-carbon backbone, the Arg 9 sidechain formed a second hydrogen bond with Tyr37. All other existing interactions remained essentially the same.

The refinement provided the refined TA1-C9 complex models shown in FIGS. 7A–7F.

TA1 and C9 contact residues were visible in the refined models depicted in FIGS. 7A–7F. Below there follows a description of contact and non-contact residues in TA1 and C9.

1) Arg9 (C9), Tyr37 (TA1) and Arg55 (TA1) Contact Residues. As can be seen in FIG. 7C, Arg9 (C9), Tyr37 (TA1) and Arg55 (TA1) residues each form hydrogen bonds. In C9, all mutations at the Arg9 position eliminated binding. Even replacement with Lys, a conservative amino acid change that essentially preserves sidechain charge and volume, still eliminated binding.

By altering the Tyr37 contact residue to Phe, there resulted a 50% reduction in specific binding affinity, whereas the Arg55 contact residue, when mutated to Lys, resulted in a 70% reduction in affinity. Both mutations conserved overall volume but changed chemical groups on the sidechains. These sidechains apparently participated in hydrogen bonding with Arg9 of the C9 antigen. As can be seen in FIG. 1, the contact residues fell within the variable L1 and L2 positions of the antibody, and are not located at positions which define canonical loop structure (see e.g., Chothia et. al., 1989 supra; and Jeffrey and Saenger (1991) for a discussion about variable positions and loops). Accordingly, these contact residues were apparently important for determining TA1 binding specificity.

2) Gly8 (C9) Contact Residue and Interactions with the TA1 Binding Cleft.

The model showed that Gly8 in the C9 peptide did not directly interact with the antibody. Nonetheless, the binding data presented in Example 3 indicated that the residue is integral for C9 recognition: the Gly8Ala mutation in C9 eliminated TA1 binding. The Gtl:Ala mutation is conservative (see Fib. 15A, 15B) since the Ala sidechain occupies a volume only slightly larger than the Gly sidechain. It seems that spatial restrictions within the TA1 binding cleft required the C9 α-carbon backbone to assume a sharp bend at this position; such a dihedral angle was apparently only allowed by the unaltered contact residue (Gly).

3) Glu7 (C9) Contact Residue Does Not Interact with TA1 Antibody.

Figure 7A:
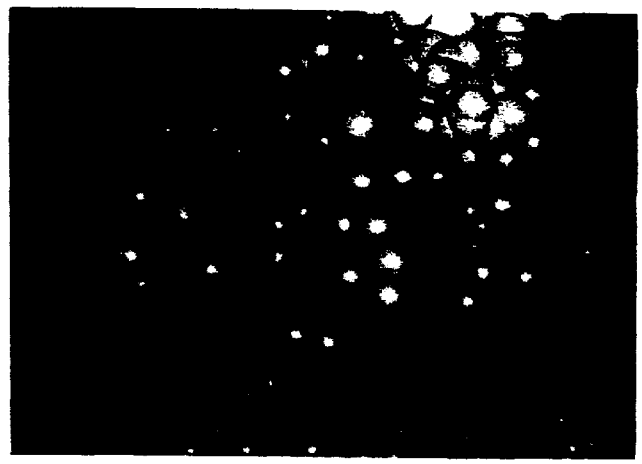
Figure 7B:
Figure 7C:

The Glu sidechain lies in a crease between L3 and L1 (see FIGS. 7A and 7B). In this position, the sidechain lies outside of the spatial constraints of the TA1 binding cleft. This observation was consistent with the binding results for the altered C9 peptide with Ala at position 7. The Ala substitution decreased sidechain volume and removed charge, the Gln substitution conserves sidechain volume and neutralizes charge, and the Lys substitution increased sidechain volume and changes charge. However, all the substitutions resulted in unchanged binding, indicating that volume changes or changes in charge at this position were tolerated because of lack of spatial restriction. Yet, the Asp mutation decreased sidechain volume but conserved negative charge, resulting in decreased binding. This result indicated that a charge repelling effect or bumping was apparently present when the sidechain was constrained closer to the C9 backbone.

4) Ile6 (C9) Residue is a Conformational Residue for the C9 Backbone.

Mutation of the Ile6 position indicated that this residue was involved in the topography of the TA1-C9 binding surface. It seems that the Ile sidechain cannot participate in hydrogen bonding since it has an aliphatic sidechain (Jeffrey and Saenger, Hydrogen Bonding in Biological Structures, pp. 351–393, Springer-Verlag, Berlin 1991); instead the residue appears to repel water from the interacting surfaces. However, when the Ile6 residue was mutated to Leu (a mutation which essentially conserves sidechain volume), decreased binding was observed, and when mutated to Val, (a mutation which decreases sidechain volume), increased binding was seen.

Comparison of the branching pattern of the Leu and Val sidechains showed that Val, which branches at the first carbon off the a carbon, more closely resembles the Ile sidechain structure than Leu, which branches at the second carbon off the a carbon. Further, in an in-silico experiment in which the Ile was substituted with each of the mutations, a smaller conformational change in C9 was seen with the Val mutation than with Leu. The Ile sidechain apparently held the C9 backbone by constraining its aliphatic group close to the α-carbon backbone and thus by occupying space, keeping the carboxy terminal end of C9 extended away from the backbone.

5) Ala5 (C9) is both a Contact and a Conformational Residue

Figure 7D:
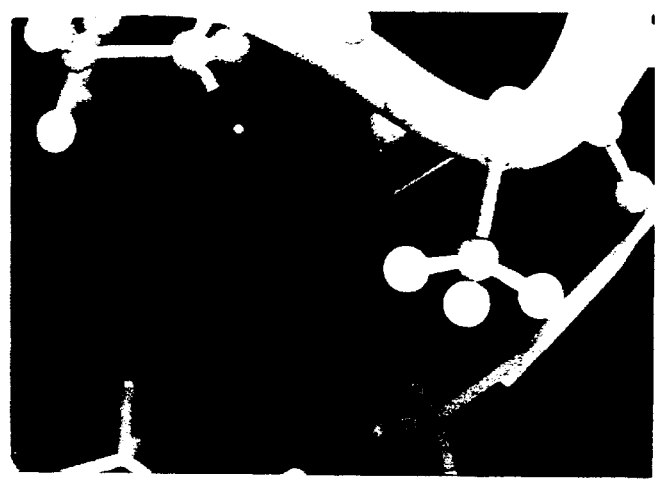

Ala5 interactions in the C9 peptide are depicted in FIG. 7D. The Western blot, competition EIA and BIAcore data all indicated that altering the Ala5 contact residue influenced the stability of the TA1-C9 complex in more than one way. For example, Western blot and competition EIA results each show similar binding trends however, the BIAcore results do not. This result, taken with the Ala5Gly result, indicates Ala5 may play a one or possibly two roles in the TA1-C9 complex. This could be due to different conditions employed in the Western blot, competition EIA and Biocore assays. For example, it is possible that the Cys mutation could be causing protein aggregation under the non-denaturing conditions of the assays, thereby blocking the epitope from binding the TA1 antibody. Differences in binding affinity may therefore be more accurately depicted by the Western blot (reducing conditions).

However, it is also possible that the Ala5 residue plays both a contact and conformational residue. The Ser and Cys mutations, which mimic Ala sidechain volume, still show some binding while the Gly mutation (reduces sidechain volume) eliminates binding. Since the Ala sidechain is not a likely hydrogen bonding partner, the result suggests that it either plays a conformational role for the C9 backbone (or a water exclusion role), or provides the necessary volume at the binding interface to allow VDW forces to act.

To investigate potential hydrogen bond formation between the Ala backbone amine and Trp164 in H2 in TA1, the Trp164Tyr mutation was made in TA1 (see e.g., FIG. 7D). While this mutation conserved some volume it apparently removes a hydrogen bonding partner, resulting in reduced binding. The position of Trp164 is not a canonical structure determinant for H2 but it is located at the junction between H2 and FR2 and may define a take-off angle of the H2 loop from the framework and influence TA1 binding site topography.

Figure 7E:
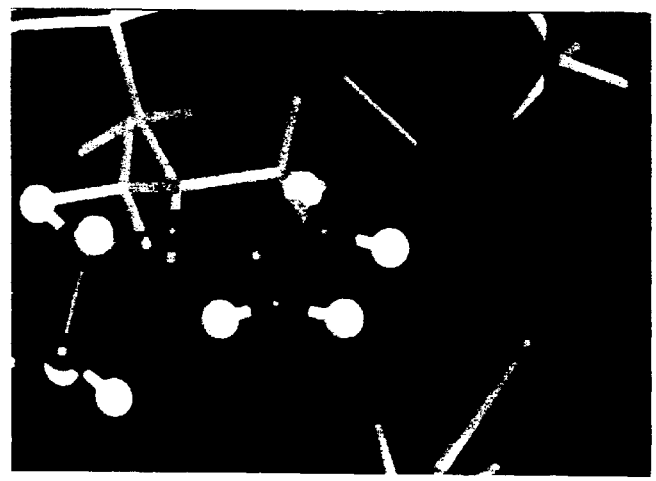
Figure 7F:
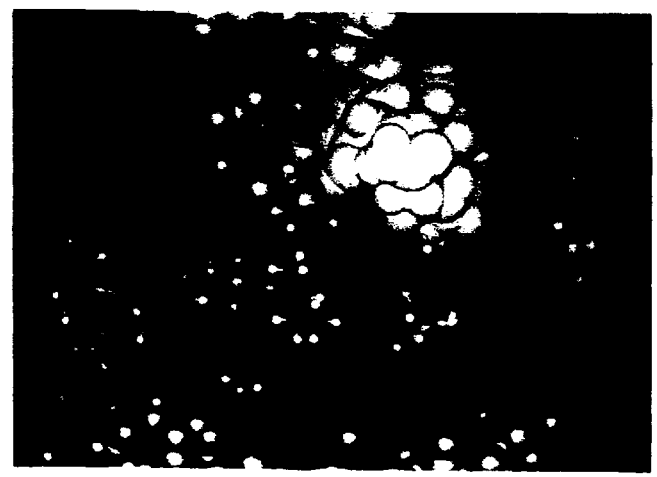

6) Arg4 (C9) Contact Residue Sidechain Forms a Hydrogen Bond with the His96 (TA1) Contact Residue The interaction between Arg4 of C9 and His96 of the TA1 antibody is represented in FIG. 7E. It was found that altering the C9 peptide to Ala or Lys at position #4 resulted in a 50% and 10% decrease in binding, respectively. These results indicated that the hydrogen bond interaction partially contributes to binding affinity between C9 and the TA1 antibody.

The His96Ala mutation in L3 of TA1 resulted in binding knockout. This result appears to be due to perturbation of the loop conformation rather than just to modification of an antigen contact residue. His96 is in a canonical loop defining region and is adjacent to a primary residue which defines canonical class. The interaction could be more completely confirmed by designing a more conservative mutation for His 96 in L3, e.g., Lys or Arg.

7) Asp1, Ser2 and Asp3 in C9 are Not Contact Residues and are Not Included in the TA1 Binding Cleft The binding affinity of mutated C9 peptides with independent Asp1, Ser2, and Asp3 mutations demonstrated that these residues did not interact with TA1. The positioning of these residues in relation to TA1 was also probed by sequentially replacing the residues with Trp. These results indicated that binding becomes progressively worse as the Trp was placed closer to the carboxy terminus (see e.g., FIGS. 7A and 7B). Other mutations in this region, including Asp1 and Asp3 mutated to Asn and Asp1 mutated to Pro, resulted in no negative effect on binding, further indicating that this region of C9 does not interact directly with TA1 nor does it play a role in C9 presentation to the binding cleft.

EXAMPLE 8

Preparation of Altered TA1 Antibodies with modified binding affinity.

To prepare a mutated TA1 antibody with increased specific binding affinity for the C9 peptide, site directed mutagenesis was performed on TA1 $V_H$ or $V_L$ DNA (see FIG. 1 (SEQ ID NO: 40) and FIG. 2 (SEQ ID NO: 42) ) at each nucleotide triplet encoding a TA1 contact residue identified by the above-described methods. DNA encoding the mutagenized TA1 contact residue was individually recombined with vectors carrying heavy chain (HC) or light chain (LC) genes (see e.g., FIGS. 3A and 3B). The resulting DNA vectors, when suitably co-expressed in an appropriate mammalian cell line and screened resulted in improved TA1 antibodies with increased specific binding affinity for C9.

Figure 3B:
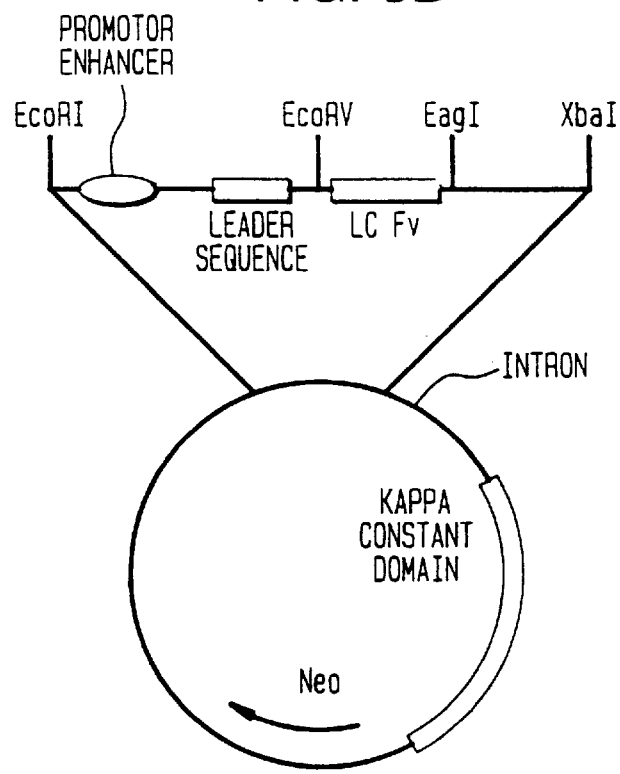

Specifically, to prepare the mutated TA1 antibodies, a set of conventional anti-digoxin IgG$_{2B}$ heavy chain (HC) and κ light chain (LC) antibody gene vectors were employed (Near et al. (1993) supra; Near et al. (1990) supra). As is illustrated in FIGS. 3A and 3B, the vectors were mutated by introducing Eco RV and EagI sites via site directed mutagenesis so that the anti-digoxin heavy and light chain $F_v$ coding regions could be replaced with the TA1 HC and LC $F_v$ genes.

First, the three Eco RV sites in the vectors were eliminated. An Eco RV restriction site was introduced 15 bases upstream of the first FR1 and an EagI restriction site 7 bases downstream of the last codon of Fr4, in the intron splicing region. The anti-digoxin κ LC gen vector was modified using overlapping PCR (Horton R. M. et al. *Gene* 77: 61 (1989)). An EcoRV restriction site was introduced 16 bases upstream of the first codon of FRI and an Eag I restriction site 3 bases downstream of the last codon of FR4, in the intron splicing region. Upstream and downstream primers were synthesized which spanned each of the two areas where the EcoRV and Eag I sites were to be introduced and containing the two restriction sites. PCR reactions were performed using the anti-digoxin κ LC gene vector template and an upstream primer spanning the Xba I site and the downstream EcoRV site containing primer, the upstream EcoRV site containing primer and the downstream EagI site containing primer, and the upstream EagI site containing primer and a downstream primer spanning the area of the Eco RI site. Three PCR DNA fragments were produced and overlapped in a following PCR reaction to form the full length gene from XbaI to Eco RI containing the Eco Rv and EagI sites. This PCR product was cloned as an XbaI-Eco RI cassette back into the anti-digoxin κ LC gene vector.

An overlapping PCR protocol (Horton R. M. et. al., (1989)(supra)) was used to create specific mutations within the CDR regions of TA1. The oligonucleotide primers used are shown in FIG. 14 (SEQ ID NOs: 26–39:); these spanned the codon sequences encoding the contact residues to be mutated. A set of PCR reactions were performed using the TA1 antibody gene template and either of two upstream primers containing the EcoRV site followed by 15 bases (for HC) or 16 bases (for LC) upstream of the first codon of FR1 followed by the first 5 codons of TA1 $V_H$ or $V_L$ and the downstream primers containing the specific mutations. A second set of reactions were performed using the upstream primers containing the specific mutations and either of two downstream primers containing the last 5 codons of TA1 $V_H$ or $V_L$ followed by 7 bases (for HC) or 3 bases (for LC) downstream of FR4 followed by the EagI site. Two sets of PCR fragments were produced and overlapped respectively in the following PCR reaction to form the full length TA1 $V_H$ or $V_L$ functional gene flanked by EcoRV and EagI restriction sites and containing the specific mutations. The resulting PCR products were cloned as EcoRV-EagI cassettes into the modified anti-digoxin $IgG_{2B}$ HC and K LC gene vectors. The resulting plasmids were used to transform strain XL1 blue (endA hsdR−HsdM+lacZΔm15 recA $lacI^q$ F', available from Stratagene). The final DNA vector constructs containing TA1 $V_H$ or $V_L$ genes with flanking constant and intron splicing regions were then subcloned in a suitable orientation as XbaI cassettes (for HC) or EcoRI/XbaI cassettes (for LC) into pSVgpt/26–10$V_H$ or pneo/26–10VL respectively (designated HC weight and LC weight.

The resulting plasmids were used to transform strain DG103 (endA thil hsdR supE44 $lacI^q$ lacZΔm15 $F^-$dam13::Tm9) obtained from D. Gelfand. Alternatively, other suitable $dam^-$ hosts can be used. The resulting vectors were HC weight and LC weight transfected into suitable mammalian cells (e.g. NSO cells) in accordance with a standard transfection and expression procedures (Near, R. I. et. al., (1990 (supra). Briefly, 10 μg of each plasmid was linearized with EcoRI and transfected into $1\times10^7$ Nso cells in 0.8 mL PBS by electroporation at 250V and 960 μFD. After 24 hours the transfected cells were placed under selective growth media: 1.2mg/mL mycophenolic acid and 1× hypoxanthine (for HC) or 1.2 mg/mL G418 (for LC). Resulting colonies were screened for $IgG_{2B}$ or κ chain expression. Those that were positive were expanded and cotransfected with the TA1 $IgG_{2B}$(wt) or κ chain(wt) counterpart and screened for $IgG_{2B}$ and κ chain production. Positive colonies were expanded and the antibodies were purified by Protein A affinity chromatography from conditioned media and assayed by the BlAcore and EIA tests disclosed herein.

Below, there follows a description of the specific binding affinity of mutated TA1 antibodies made in accordance with the methods disclosed herein:

1) Improved TA1 antibodies Tyr213Phe and Tyr218Phe showed an increase in specific binding affinity.

Independently changing the two Tyr residues in H3 to a more hydrophobic Phe residue conserved the combining site topography and apparently caused H3, upon C9 peptide binding, to associate with Arg9 of C9 with greater surface area contact. Here, and without the use of X-ray crystallography, we have improved the specific binding affinity of the TA1 antibody by engineering the antibody to include new contact residues that increase specific binding affinity. See also, FIG. 11. It is likely that by combining the two mutations in a single TA1 antibody, an even greater increase in specific binding could be achieved.

2) Mutated TA1 antibody Leu30Ala (control) showed a decrease in specific binding affinity.

This mutated TA1 antibody was designed as a positive control. As is apparent from the previous discussion, Leu3O falls within a region which defines a canonical loop structure and is directly adjacent to position 29 in L1. This residue is a primary residue for defining L1 canonical class (see e.g., Chothia et. al., *Nature* 342:877–883, 1989). Mutation at this site demonstrated the degree to which overall binding can be effected by a moderately conservative change (a decrease in sidechain volume) in a region which defines loop conformation, even though the position was quite distant from the predicted antigen contact residues. See also, FIG. 11.

3) Improved TA1 Antibody Phe99Tyr shows an increase in specific binding affinity.

This mutated TA1 antibody was originally designed as a negative control, since the residue was predicted to have no contact with the C9 peptide. However, an Ala mutation showed a 90% drop in binding. Apparently, this effect was due to a change in the binding site topography caused by the radical decrease in sidechain volume.

Mutation of the Phe99 with a more conservative replacement, Tyr, gave surprising results: a 20% increase in binding. It seems that improved binding is due to a change in the overall L3 structure which apparently increases interface surface area. Alternatively, the Phe to Tyr mutation in this position, while still maintaining much hydrophobic character, contributed aromatic hydrogen bonding (Kelley and O'Connell, *Biochem.* 32:6828–6835, 1993). Without wishing to be bound by any particular theory, this could force C9 into a more favorable binding interface with the L1, L2, and H3 regions of the TA1 antibody. See also, FIG. 11.

It will be apparent that the TA1 antibody and/or one or more of the improved TA1 antibodies disclosed herein can be used in a kit for the detection of prothrombin activation in a research or clinical setting. Such a kit would suitably include: 1) TA1 antibody and/or improved TA1 antibodies in a suitable buffer solution 2) prothrombin and/or the F1.2 peptide in a suitable buffer and 3) directions for using the kit. Suitable buffer systems for use with the kit have been disclosed, e.g. in Harlow and Lane, supra.

All publications and patent applications mentioned in the specification are indicative of the level of skill of those in the art to which this invention pertains. All disclosed publications and patent applications are fully incorporated herein by reference to the same extent as if each individual publication or patent application were specifically and individually stated to be incorporated by reference.

Although the foregoing inventions have been described in some detail by way of illustration and example for the purposes of clarity of understanding, one skilled in the art will easily ascertain that certain changes and modifications may be practiced without departing from the spirit and scope of the appended claims.

What is claimed is:

1. An antibody or F1.2 binding fragment thereof comprising the TA1 $V_H$ region of FIG. 2 (SEQ ID NO: 43) and the TA1 $V_L$ region of FIG. 1 (SEQ ID NO: 41).

2. An antibody or F1.2 binding fragment thereof comprising the TA1 $V_H$ region of FIG. 2 (SEQ ID NO: 43) and the TA1 $V_L$ region of FIG. 1 (SEQ ID NO: 41); wherein the TA1 $V_L$ region consists of a tyrosine at position 99.

3. An antibody or F1.2-binding fragment thereof comprising the TA1 $V_H$ region of FIG. 2 (SEQ ID NO: 43) and the TA1 $V_L$ region of FIG. 1 (SEQ ID NO: 41); wherein the TA1 $V_H$ region consists of a phenylalanine at position 99 or 104.

4. A kit for detecting prothrombin activation in a biological sample comprising the antibody or fragment of claim 1, 2, or 3.

* * * * *

```
                            SEQUENCE LISTING (1) GENERAL INFORMATION:

(iii) NUMBER OF SEQUENCES: 49

(2) INFORMATION FOR SEQ ID NO:1:

(i) SEQUENCE CHARACTERISTICS:
          (A) LENGTH: 43 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

CCATGGGCAT CTGACCGTGC AATCGAAGGT CGTTGAGGGA TCC                           43

(2) INFORMATION FOR SEQ ID NO:2:

(i) SEQUENCE CHARACTERISTICS:
          (A) LENGTH: 43 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

CCATGGGACG CTGACCGTGC AATCGAAGGT CGTTGAGGGA TCC                           43

(2) INFORMATION FOR SEQ ID NO:3:

(i) SEQUENCE CHARACTERISTICS:
          (A) LENGTH: 43 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO
```

(v) FRAGMENT TYPE:

(vi) ORIGINAL SOURCE:

(xi) SEQUENCE DESCRIPTION: SEQ ID NO:3:

CCATGGGACT CTGCACGTGC AATCGAAGGT CGTTGAGGGA TCC        43

(2) INFORMATION FOR SEQ ID NO:4:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

CCATGGGACT CTGACGCTGC AATCGAAGGT CGTTGAGGGA TCC        43

(2) INFORMATION FOR SEQ ID NO:5:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

CCATGGGACT CTGACCGTTC CATCGAAGGT CGTTGAGGGA TCC        43

(2) INFORMATION FOR SEQ ID NO:6:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

CCATGGGACT CTGACCGTGC AGCTGAAGGT CGTTGAGGGA TCC        43

(2) INFORMATION FOR SEQ ID NO:7:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

CCATGGGACT CTGACCGTGC TATCGCTGGT CGTTGAGGGA TCC        43

(2) INFORMATION FOR SEQ ID NO:8:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:

CCATGGGACT CTGACCGTGC AATCGAAGCA CGTTGAGGGA TCC        43

(2) INFORMATION FOR SEQ ID NO:9:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

CCATGGGACT CTGACCGTGC AATCGAAGGT GCATGAGGGA TCC        43

(2) INFORMATION FOR SEQ ID NO:10:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:10:

CCATGGGCTG CTGCTGCTGC TATCGCTGGC CGTTGAGGGA TCC                         43

(2) INFORMATION FOR SEQ ID NO:11:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:11:

CCATGGGACT CTGACCGTGC TATCGAAGGT AAATGAGGGA TCC                         43

(2) INFORMATION FOR SEQ ID NO:12:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:12:

CCATGGGACT CTGACCGTGC AATCGAAGGT ATCTGAGGGA TCC                         43

(2) INFORMATION FOR SEQ ID NO:13:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:13:

CCATGGGACT CTGACCGTGC TATCCAGGGT CGTTGAGGGA TCC								43

(2) INFORMATION FOR SEQ ID NO:14:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:14:

CCATGGGACT CTGACCGTGC TATCGACGGT CGTTGAGGGA TCC								43

(2) INFORMATION FOR SEQ ID NO:15:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:15:

CCATGGGACT CTGACCGTGC AATCAAAGGT CGTTGAGGGA TCC								43

(2) INFORMATION FOR SEQ ID NO:16:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:16:

CCATGGGACT CTGACCGTGC ACTGGAAGGT CGTTGAGGGA TCC								43

(2) INFORMATION FOR SEQ ID NO:17:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:17:

CCATGGGACT CTGACCGTGC AGTTGAAGGT CGTTGAGGGA TCC                43

(2) INFORMATION FOR SEQ ID NO:18:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:18:

CCATGGGACT CTGACCGTGG TATCGAAGGT CGTTGAGGGA TCC                43

(2) INFORMATION FOR SEQ ID NO:19:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:19:

CCATGGGACT CTGACCGTTG CATCGAAGGT CGTTGAGGGA TCC                43

(2) INFORMATION FOR SEQ ID NO:20:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:20:

CCATGGGACT CTGACAAAGC AATCGAAGGT CGTTGAGGGA TCC                          43

(2) INFORMATION FOR SEQ ID NO:21:

(i) SEQUENCE CHARACTERISTICS:
             (A) LENGTH: 43 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:21:

CCATGGAACT CTAACCGTGC AATCGAAGGT CGTTGAGGGA TCC                          43

(2) INFORMATION FOR SEQ ID NO:22:

(i) SEQUENCE CHARACTERISTICS:
             (A) LENGTH: 43 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:22:

CCATGGTGGT CTGACCGTGC AATCGAAGGT CGTTGAGGGA TCC                          43

(2) INFORMATION FOR SEQ ID NO:23:

(i) SEQUENCE CHARACTERISTICS:
             (A) LENGTH: 43 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:23:

CCATGGGACT GGGACCGTGC AATCGAAGGT CGTTGAGGGA TCC                          43

(2) INFORMATION FOR SEQ ID NO:24:

(i) SEQUENCE CHARACTERISTICS:
             (A) LENGTH: 43 base pairs (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:24:

CCATGGGACT CTTGGCGTGC AATCGAAGGT CGTTGAGGGA TCC                43

(2) INFORMATION FOR SEQ ID NO:25:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:25:

CCATGGCCGT CTGACCGTGC AATCGAAGGT CGTTGAGGGA TCC                43

(2) INFORMATION FOR SEQ ID NO:26:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:26:

GGCCTGGAGT GGATTGGAGC GATTGATCCT GATAATGGT                     39

(2) INFORMATION FOR SEQ ID NO:27:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:27:

GTCTATTACT GTGACTACGC TAGGTTCGAC GACTATGCT                                    39

(2) INFORMATION FOR SEQ ID NO:28:

(i) SEQUENCE CHARACTERISTICS:
             (A) LENGTH: 39 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:28:

CATAGTAATG GCAACACTGC CTTGTATTGG TTCCTGCAG                                    39

(2) INFORMATION FOR SEQ ID NO:29:

(i) SEQUENCE CHARACTERISTICS:
             (A) LENGTH: 39 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:29:

CCTCAGCTCC TGATATATGC GATGTCCAAC CTTGCCTCA                                    39

(2) INFORMATION FOR SEQ ID NO:30:

(i) SEQUENCE CHARACTERISTICS:
             (A) LENGTH: 40 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:30:

GTTTATTACT GTTTTGCAGG CTCTAGAATT TCCGCTCACG                                   40

(2) INFORMATION FOR SEQ ID NO:31:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:31:

TGTTTGCAGC ATCTAGAATG GCCGCTCACG TTCGGTGCT                                    39

(2) INFORMATION FOR SEQ ID NO:32:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:32:

TGTTTGCAGC ATCTAGAAGC TCCGCTCACG TTCGGTGCT                                    39

(2) INFORMATION FOR SEQ ID NO:33:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:33:

TGTGACTACT TCAGGTTCGA C                                                      21

(2) INFORMATION FOR SEQ ID NO:34:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:34:

TGGATTGGAT ATATTGATCT T                                                      21

(2) INFORMATION FOR SEQ ID NO:35:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:35:

CTGATATATA AGATGTCCAA C                                                      21

(2) INFORMATION FOR SEQ ID NO:36:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:36:

GGTAACACTT TCTTGTATTG G                                                      21

(2) INFORMATION FOR SEQ ID NO:37:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:37:

AAGAGTCTCG CTCATAGTAA T                                                      21

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:38:

CATCTAGAAT ATCCGCTCAC G                                  21

(2) INFORMATION FOR SEQ ID NO:39:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:39:

TTCGACGACT TCGCTGTGGA C                                  21

(2) INFORMATION FOR SEQ ID NO:40:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
        (B) LOCATION: 30
        (D) OTHER INFORMATION: Xaa is Leu or Ala
        (B) LOCATION: 37
        (D) OTHER INFORMATION: Xaa is Tyr, Ala or Phe
        (B) LOCATION: 55
        (D) OTHER INFORMATION: Xaa is Arg, Ala, or Lys
        (B) LOCATION: 96
        (D) OTHER INFORMATION: Xaa is His or Ala
        (B) LOCATION: 99
        (D) OTHER INFORMATION: Xaa is Phe, Ala or Tyr
        (A) NAME/KEY: Coding Sequence
        (B) LOCATION: 22...371

(D) OTHER INFORMATION: EXON 1

(xi) SEQUENCE DESCRIPTION: SEQ ID NO:40:

```
GATATCTTCA GCTTCCAGCA GT GAT ATT GTG ATG ACT CAG GCT GCA CCC TCA          52
                        Asp Ile Val Met Thr Gln Ala Ala Pro Ser
                         1               5                  10

ATA CCT GTC ACT CCT GGA GAG TCA GTA TCC ATC TCC TGC AGG TCT AGT          100
Ile Pro Val Thr Pro Gly Glu Ser Val Ser Ile Ser Cys Arg Ser Ser
                15                  20                  25

AAG AGT CTC BYN CAT AGT AAT GGC AAC ACT KHN TTG TAT TGG TTC CTG          148
Lys Ser Leu Xaa His Ser Asn Gly Asn Thr Xaa Leu Tyr Trp Phe Leu
            30                  35                  40

CAG AGG CCA GGC CAG TCT CCT CAG CTC CTG ATA TAT VVN ATG TCC AAC          196
Gln Arg Pro Gly Gln Ser Pro Gln Leu Leu Ile Tyr Xaa Met Ser Asn
                45                  50                  55

CTT GCC TCA GGA GTC CTA GGC AGG GTC AGT GGC AGT GGG TCA GGA ACT          244
Leu Ala Ser Gly Val Leu Gly Arg Val Ser Gly Ser Gly Ser Gly Thr
                60                  65                  70

GAT TTC ACA CTG AGA ATC AGT AGA GTG GAG GCT GAG GAT ATG GGT GTT          292
Asp Phe Thr Leu Arg Ile Ser Arg Val Glu Ala Glu Asp Met Gly Val
 75              80                  85                  90

TAT TAC TGT TTG CAG SMN CTA GAA KHN CCG CTC ACG TTC GGT GCT GGG          340
Tyr Tyr Cys Leu Gln Xaa Leu Glu Xaa Pro Leu Thr Phe Gly Ala Gly
                95                 100                 105

ACC AGG CTG GAG CTG AAA CGT AAG TAGCGGCCG                                373
Thr Arg Leu Glu Leu Lys Arg Lys
                110
```

(2) INFORMATION FOR SEQ ID NO:41:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(ix) FEATURE:
        (B) LOCATION: 30
        (D) OTHER INFORMATION: Xaa is Leu or Ala
        (B) LOCATION: 37
        (D) OTHER INFORMATION: Xaa is Tyr, Ala or Phe
        (B) LOCATION: 55
        (D) OTHER INFORMATION: Xaa is Arg, Ala, or Lys
        (B) LOCATION: 96
        (D) OTHER INFORMATION: Xaa is His or Ala
        (B) LOCATION: 99
        (D) OTHER INFORMATION: Xaa is Phe, Ala or Tyr (xi) SEQUENCE DESCRIPTION: SEQ ID NO:41:

```
Asp Ile Val Met Thr Gln Ala Ala Pro Ser Ile Pro Val Thr Pro Gly
 1               5                  10                  15

Glu Ser Val Ser Ile Ser Cys Arg Ser Ser Lys Ser Leu Xaa His Ser
                20                  25                  30

Asn Gly Asn Thr Xaa Leu Tyr Trp Phe Leu Gln Arg Pro Gly Gln Ser
            35                  40                  45

Pro Gln Leu Leu Ile Tyr Xaa Met Ser Asn Leu Ala Ser Gly Val Leu
```

```
            50                  55                  60
Gly Arg Val Ser Gly Ser Gly Ser Gly Thr Asp Phe Thr Leu Arg Ile
 65                  70                  75                  80

Ser Arg Val Glu Ala Glu Asp Met Gly Val Tyr Tyr Cys Leu Gln Xaa
                 85                  90                  95

Leu Glu Xaa Pro Leu Thr Phe Gly Ala Gly Thr Arg Leu Glu Leu Lys
             100                 105                 110

Arg Lys
```

(2) INFORMATION FOR SEQ ID NO:42:

(i) SEQUENCE CHARACTERISTICS:
        (A) LENGTH: 385 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
        (B) LOCATION: 50
        (D) OTHER INFORMATION: Xaa is Trp, Ala, or Tyr
        (B) LOCATION: 99
        (D) OTHER INFORMATION: Xaa is Tyr, Ala or Phe
        (B) LOCATION: 104
        (D) OTHER INFORMATION: Xaa is Tyr or Phe
        (A) NAME/KEY: Coding Sequence
        (B) LOCATION: 23...363
        (D) OTHER INFORMATION: EXON 1

(xi) SEQUENCE DESCRIPTION: SEQ ID NO:42:

```
GATATCACAG GTGTCCTCTC T GAG GTT CAG CTG CAG CAG TCT GGG GCT  GAG         51
                        Glu Val Gln Leu Gln Gln Ser Gly Ala  Glu
                         1               5                    10

CTT GTG AGG CCA GGG GCC TTA GTC AAG TTG TCC TGC AAA GCT TCT GGC          99
Leu Val Arg Pro Gly Ala Leu Val Lys Leu Ser Cys Lys Ala Ser Gly
             15                  20                  25

TTC AAC ATT AAA GAC TAC TAT ATG CAC TGG GTG AAG CAG AGG CCT GAA         147
Phe Asn Ile Lys Asp Tyr Tyr Met His Trp Val Lys Gln Arg Pro Glu
             30                  35                  40

CAG GGC CTG GAG TGG ATT GGA KVN ATT GAT CCT GAT AAT GGT GAA ACT         195
Gln Gly Leu Glu Trp Ile Gly Xaa Ile Asp Pro Asp Asn Gly Glu Thr
         45                  50                  55

ATA TAT GAC CCG AAG TTT CAG GGC AAG GCC AGT ATA ACA GCA GAC ACA         243
Ile Tyr Asp Pro Lys Phe Gln Gly Lys Ala Ser Ile Thr Ala Asp Thr
     60                  65                  70

TCT TCC AAC ACA GCC TAT CTG CAG CTC AGC AGC CTG ACA TCT GAG GAC         291
Ser Ser Asn Thr Ala Tyr Leu Gln Leu Ser Ser Leu Thr Ser Glu Asp
 75                  80                  85                  90

ACT GCC GTC TAT TAC TGT GAC TAC KHN AGG TTC GAC GAC TWY GCT GTG         339
Thr Ala Val Tyr Tyr Cys Asp Tyr Xaa Arg Phe Asp Asp Xaa Ala Val
                 95                 100                 105

GAC TAC TGG GGT ACC TCA GTC ACC GTC TCC TCA GGTAAGACG GCCG              385
Asp Tyr Trp Gly Thr Ser Val Thr Val Ser Ser
             110                 115
```

(2) INFORMATION FOR SEQ ID NO:43:

```
    (i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(ix) FEATURE:
        (B) LOCATION: 50
        (D) OTHER INFORMATION: Xaa is Trp, Ala, or Tyr
        (B) LOCATION: 99
        (D) OTHER INFORMATION: Xaa is Tyr, Ala or Phe
        (B) LOCATION: 104
        (D) OTHER INFORMATION: Xaa is Tyr or Phe (xi) SEQUENCE DESCRIPTION: SEQ ID NO:43:
```

Glu Val Gln Leu Gln Gln Ser Gly Ala Glu Leu Val Arg Pro Gly Ala
 1               5                  10                  15

Leu Val Lys Leu Ser Cys Lys Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Xaa Ile Asp Pro Asp Asn Gly Glu Thr Ile Tyr Asp Pro Lys Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asp Tyr Xaa Arg Phe Asp Asp Xaa Ala Val Asp Tyr Trp Gly Thr Ser
            100                 105                 110

Val Thr Val Ser Ser
        115

```
(2) INFORMATION FOR SEQ ID NO:44:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:44:
```

GGAAGCTTAT GAAAAAAATA CCTC                                                24

```
(2) INFORMATION FOR SEQ ID NO:45:

(i) SEQUENCE CHARACTERISTICS:
        (A) LENGTH: 34 base pairs
```

(B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:45:

GGGGATCCCT CACCATGGTT CCTTCTTTCT GTTC                                34

(2) INFORMATION FOR SEQ ID NO:46:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:46:

CATGGGACTC TGACCGTGCA ATCGAAGGTC GTTGAGGGAT CCGGTAC                  47

(2) INFORMATION FOR SEQ ID NO:47:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:47:

CGGATCCCTC AACGACCTTC GATTGCACGG TCAGAGTCC                           39

(2) INFORMATION FOR SEQ ID NO:48:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO

```
        (v) FRAGMENT TYPE: N-terminal (vi) ORIGINAL SOURCE:

(xi) SEQUENCE DESCRIPTION: SEQ ID NO:48:

Asp Ser Asp Arg Ala Ile Glu Gly Arg
 1               5

(2) INFORMATION FOR SEQ ID NO:49:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (v) FRAGMENT TYPE: N-terminal (ix) FEATURE:
            (A) NAME/KEY:
            (B) LOCATION: 1...1
            (D) OTHER INFORMATION: Xaa is Ala
            (A) NAME/KEY:
            (B) LOCATION: 2...2
            (D) OTHER INFORMATION: Xaa is Ala
            (A) NAME/KEY:
            (B) LOCATION: 3...3
            (D) OTHER INFORMATION: Xaa is Ala
            (A) NAME/KEY:
            (B) LOCATION: 4...4
            (D) OTHER INFORMATION: Xaa is Ala
            (A) NAME/KEY:
            (B) LOCATION: 7...7
            (D) OTHER INFORMATION: Xaa is Ala (xi) SEQUENCE DESCRIPTION: SEQ ID NO:49:

Xaa Xaa Xaa Xaa Ala Ile Xaa Gly Arg
 1               5
```